(12) United States Patent
Huang

(10) Patent No.: US 7,144,701 B2
(45) Date of Patent: *Dec. 5, 2006

(54) HIGH-THROUGHPUT METHODS FOR DETECTING DNA METHYLATION

(75) Inventor: Tim Hui-Ming Huang, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 222 days.

This patent is subject to a terminal disclaimer.

(21) Appl. No.: 10/081,327

(22) Filed: Feb. 21, 2002

(65) Prior Publication Data

US 2003/0129602 A1 Jul. 10, 2003

Related U.S. Application Data

(63) Continuation of application No. 09/497,855, filed on Feb. 4, 2000, now Pat. No. 6,605,432.

(60) Provisional application No. 60/120,592, filed on Feb. 18, 1999, provisional application No. 60/118,760, filed on Feb. 5, 1999.

(51) Int. Cl.
*C07H 21/04* (2006.01)
*C12Q 1/68* (2006.01)

(52) U.S. Cl. .................. 435/6; 435/91.2; 435/287.2; 536/23.1

(58) Field of Classification Search .................. 435/6, 435/91.1, 91.2, 287; 536/23.1, 24.3
See application file for complete search history.

(56) References Cited

U.S. PATENT DOCUMENTS

| | | | |
|---|---|---|---|
| 4,682,195 A | | 7/1987 | Yilmaz |
| 4,683,202 A | | 7/1987 | Mullis |
| 4,800,159 A | | 1/1989 | Mullis et al. |
| 5,589,339 A | | 12/1996 | Hampson et al. |
| 5,591,575 A | | 1/1997 | Hampson et al. |
| 5,786,146 A | | 7/1998 | Herman et al. |
| 5,871,917 A | * | 2/1999 | Duffy ............................ 435/6 |
| 6,027,894 A | * | 2/2000 | Sapolsky et al. .............. 435/6 |
| 6,605,432 B1 | * | 8/2003 | Huang ........................... 435/6 |

OTHER PUBLICATIONS

Cross et al. "Purification of CpG islands using a methylated DNA binding column." Nature Genetics, vol. 6, pp. 236-244, Marych 1994.*
Donini et al. "AFLP fingerprinting reveals pattern differences between template DNA extracted from different plant organs." Genome. vol. 40, pp. 521-526, 1997.*

Akopyants et al., "PCR-based Subtractive Hybridization and Differences in Gene Content Among Strains of *Helicobacter pylori*", Proc. Natl. Acad. Sci. USA, vol. 95, pp. 13108-13113, 1998.
Antequera, F., et al., "High Levels of De Novo Methylation and Altered Chromatin Structure at CpG Islands in Cell Lines", Cell, vol. 2, pp. 503-514, 1990.
Baylin et al., "Alterations in DNA Methylation: A Fundamental Aspect of Neoplasia", Advances in Cancer Research, pp. 140-196, 1998.
Baylin, Stephen B., "Tying it all Together. Epigenetics, Genetics, Cell Cycle, and Cancer", Science, vol. 277, pp. 1948-1949, 1997.
Belinsky et al., "Aberrant Methylation of $p16^{INK4a}$ is an Early Event in Lung Cancer and a Potential Biomarker for Early Diagnosis", Proc. Natl. Acad. Sci. USA, vol. 95, pp. 11891-11896, 1998.
Belinsky et al., "Increased Cytosine DNA-methyltransferase Activity is Target-cell-specific and an Early Event in Lung Cancer", Proc. Natl. Acad. Sci. USA, vol. 93, pp. 4045-4050, 1996.
Bloom, H.J.G. and Richardson, W.W., "Histological Grading and Prognosis in Breast Cancer", British Journal of Cancer, vol. 11, pp. 359-377, 1957.
Brandeis, M. et al., "Sp1 Elements Protect a CpG Island from *de novo* Methylation", Nature, vol. 371, pp. 435-438, 1994.
Carotti et al., "Influence of Pre-existing Methylation on the de Novo Activity of Eukaryotic DNA Methyltransferase", Biochem. J., vol. 37, pp. 1101-1108, 1998.
Christman et al., "5-Methyl-2'-deoxycytidine in single-stranded DNA can act in cis to Signal *de novo* DNA Methylation", Proc. Natl. Acad. Sci., USA, vol. 92, pp. 7347-7351, 1995.
Chuang et al., "Human DNA-(Cytosine-5) Methyltransferase-PCNA Complex as a Target for $^{p21WAF1}$", Science, vol. 277, pp. 1996-2000, 1997.
Craig et al., "Removal of Repetitive Sequences from FISH Probes Using PCR-Assisted Affinity Chromatography", Hum. Genet., vol. 100, pp. 472-476, 1997.
Frommer, M. et al., "A Genomic Sequencing Protocol that Yields a Positive Display of 5-Methylcytosine Residues in Individual DNA strands", Proc. Natl. Acad. Sci. USA, vol. 89, pp. 1827-1931, 1992.
Graff et al., "Mapping Patterns of CpG Island Methylation in Normal and Neoplastic Cells Implicates Both Upstream and Downstream Regions in *de novo* Methylation", J. Biol. Chem., vol. 272, No. 35, pp. 22322-22329, 1997.

(Continued)

*Primary Examiner*—Jeanine A. Goldberg
(74) *Attorney, Agent, or Firm*—Barry L. Davison; Davis Wright Tremaine

(57) ABSTRACT

The present invention provides a method of hybridization, differential methylation hybridization (DMH) for high throughput methylation analysis of multiple CpG island loci. DMH utilizes nucleic acid probes prepared from a cell sample to screen numerous CpG dinucleotide rich fragments affixed on a screening array. Positive hybridization signals indicate the presence of methylated sites. Methods of preparing the hybridization probes and screening array are also provided.

17 Claims, 11 Drawing Sheets

OTHER PUBLICATIONS

Herman et al., "Methylation-specific PCR: A Novel PCR Assay for Methylation Status of CpG Islands", Proc. Natl. Acad. Sci. USA, vol. 93, pp. 9821-9826, 1996.

Huang, T.H., et al., "Methylation Profiling of CpG Islands in Human Breast Cancer Cells", Human Molecular Genetics, vol. 8, No. 3, pp. 459-470, 1999.

Jones, P.A., "DNA Methylation Errors and Cancer", Cancer Res., vol. 56, pp. 2463-2467, 1996.

Laird et al., "DNA Methylation and Cancer", Hum. Mol. Genet., vol. 3, pp. 1487-1495, 1994.

Lee J.H. and Welch D.R., "Identification of Highly Expressed Genes in Metastasis-Suppressed Chromosome 6/Human Malignant Melanoma Hybrid Cells Using Subtractive Hybridization and Differential Display", Int. J. Cancer, vol. 71, pp. 1035-1044, 1997.

Li et al., "Role for DNA Methylation in Genomic Imprinting", Nature, vol. 366, pp. 362-365, 1993.

Mummaneni, P., et al., "Epigenetic Gene Inactivation Induced by a Cis-acting Methylation Center", J. Biol. Chem., vol. 270, No. 2, pp. 788-792, 1995.

Pfeifer, G.P., et al., "Polymerase Chain Reaction-Aided Genomic Sequencing of an X Chromosome-linked CpG Island: Methylation Patterns Suggest Clonal Inheritance, CpG Site Autonomy, and an Explanation of Activity State Stability", Proc. Natl. Acad. Sci. USA, vol. 87, pp. 8252-8256, 1990.

Saiki et al., "Primer-Directed Enzymatic Amplification of DNA with a Thermostable DNA Polymerase", Science, vol. 239, pp. 487-491, 1988.

Schena et al., "Quantitative Monitoring of Gene Expression Patterns with a Complementary DNA Microarray", Science, vol. 270, pp. 467-470, 1995.

Singer-Sam, J. and Riggs, A..D., "X-Chromosone Inactivation and DNA Methylation", DNA Methylation: Molecular Biology and Biological Significance, pp. 358-384, 1993.

Vertino et al., "De Novo Methylation of CpG Island Sequences in Human Fibroblasts Overexpressing DNA (Cytosine-5)—Methyltransferase", Mol. Cell Biol., vol. 16, pp. 4555-4565, 1996.

Wu et al., "Expression of Prokaryotic *Hhal* DNA Methyltransferase is Transforming and Lethal to NIH 3T3 Cells", Cancer Res., vol. 56, pp. 616-622, 1996.

* cited by examiner

HIGH-THROUGHPUT METHODS FOR DETECTING DNA METHYLATION

CROSS REFERENCE TO RELATED APPLICATIONS

This application is a continuation of, and claims the benefit of priority to U.S. patent application Ser. No. 09/497,855, filed 04 Feb. 2000 and of same title (now U.S. Pat. No. 6,605,432), and also claims the benefit of priority to U.S. Provisional Patent Application Ser. No. 60/120,592, filed 18 Feb. 1999 and to U.S. Provisional Patent Application Ser. No. 60/118,760, filed 05 Feb. 1999, all of which are incorporated herein by reference in their entireties.

This invention was made with Government support under National Institute of Health grant No. DHHS 5 R29 CA 69065 and U.S. Army Medical Research and Material Command grant No. DAMD 17-98-1-8214. The Government has certain rights in the invention.

FIELD OF INVENTION

The present invention relates to methods for detecting the presence or absence of methylated CpG islands within a genome utilizing a microarray based technology, Differential Methylation Hybridization (DMH). The invention is also used for identifying methylation patterns in a cell sample which may be indicative of a disease state. Also provided are methods for preparing nucleic acid fragments and nucleic acid probes to be used in said DMH methods.

BACKGROUND OF INVENTION

Epigenetic events are heritable alterations in gene function which are mediated by factors other than changes in primary DNA sequence. DNA methylation is one of the most widely studied epigenetic mechanisms and numerous studies have been conducted to determine its role in oncogenesis. DNA methylation usually occurs at cytosines located 5' of guanines, known as CpG dinucleotides, in the human genome. DNA (cytosine-5)-methyltransferase (DNA-MTase) catalyzes this reaction by adding a methyl group from S-adenosyl-L-methionine to the fifth carbon position of the cytosines. While DNA-MTase favors hemimethylated substrates for its normal maintenance activity in the cell, the enzyme also exhibits an ability to methylate CpG dinucleotides de novo. Most cytosines within the CpG dinucleotides are methylated in the human genome, but some remain unmethylated in specific CpG dinucleotide rich genomic regions, known as CpG islands. See Antequera, F. et al., Cell 62: 503–514 (1990).

Methylation of CpG islands is known to play a critical role in regulating gene expression. This effect is exerted via altering local chromatin structure and limiting the access of protein factors to initiate gene transcription. In normal cells, this epigenetic modification is associated with transcriptional silencing of imprinted genes, some repetitive elements and genes on the inactive X chromosome. See Li et al., Nature 366: 362–365 (1993); Singer-Sam, J. and Riggs A. D., (1993) In Jost, J. P., and Saluz, H. P. (eds), "DNA Methylation: Molecular Biology and Biological Significance," p.358–384. In neoplastic cells, it has been observed that the normally unmethylated CpG islands can become aberrently methylated, or hypermethylated. See Jones, P. A., Cancer Res. 56: 2463–2467 (1996); Baylin et al., Advances in Cancer Research, In Vande Woude, G. F. and Klein, G. (eds) 72: 141–196 (1997).

In addition to classic genetic mutations, hypermethylation of CpG islands is an alternative mechanism for inactivation of tumor suppressor genes and there is growing evidence that altered cytosine methylation patterns play important roles in cancer development. See e.g., Belinsky et al., 95 Proc. Natl. Acad. Sci. USA 11891–11896 (1998); Baylin et al., Advances in Cancer Research, In Vande Woude, G. F. and Klein, G. (eds.) 72: 141–196 (1997). The methylation patterns of DNA from cancer tumor cells are generally different than those of normal cells. See Laird et al., Hum. Mol. Genet. 3: 1487–1495 (1994). Tumor cell DNA is generally undermethylated relative to normal cell DNA, but selected regions of the tumor cell genome may be more methylated than the same regions of a normal cell genome. Hence, detection of altered methylation patterns in a tumor cell genome is an indication that the cell is cancerous.

Recently, the molecular mechanisms underlying CpG island hypermethylation in cancer have been explored and evidence suggests that increased DNA-MTase levels can contribute to tumorigenesis by promoting de novo methylation of CpG island sequences. See Vertino et al., Mol. Cell Biol., 16: 4555–4565 (1996); Wu et al., Cancer Res., 56: 616–622 (1996). For instance, if hypermethylation occurs in the CpG islands of genes related to growth-inhibitory activities, it may lead to associated transcriptional silencing and promote neoplastic cell proliferation. Further, recent data has shown that dysregulation of p21, a cell cycle regulator that normally modulates DNA-MTase action may also promote de novo methylation. See Chuang et al., Science 277: 1996–2000 (1997). Studies have suggested that local cis-acting signals and trans-acting factors capable of preventing specific CpG islands from de novo methylation can be disrupted in tumor cells. See Brandeis, M. et al., Nature, 371: 435–438 (1995); Mummaneni, P. et al., J. Biol. Chem., 270: 788–792 (1995); Graff et al., J. Biol. Chem., 272: 22322–22329 (1997).

Presently, there is no direct evidence that disturbances of such local factors results in de novo methylation of specific CpG islands. Rather, de novo methylation is commonly thought to be a generalized phenomenon associated with a stochastic process in tumor cells possessing aberrant DNA-MTase activities. See Jones, P. A., Cancer Res., 56, 2463–2467 (1996); Pfeifer et al., Proc. Natl. Acad. Sci. USA, 87: 8252–8256.(1990). This random methylation process can occur at CpG dinucleotide sites located within the regulatory regions of tumor suppressor genes. The progressive silencing of their transcripts may provide tumor cells with a growth advantage, and the specific hypermethylated sites observed in particular cancer types could be the result of clonal selection during tumor development.

Thus, identification of genetic changes in tumorigenesis is a major focus in molecular cancer research. However, the differences in CpG island methylation patterns between normal and cancer cells remain poorly understood.

Traditionally, methylation analysis has been carried out by Southern hybridization which assesses a few methylation-sensitive restriction sites within CpG islands of known genes. More sensitive assays for mapping DNA methylation patterns such as bisulfite DNA sequencing and methylation-specific PCR, have allowed a detailed analysis of multiple CpG dinucleotides across a single CpG island of interest. Bisulfite DNA sequencing utilizes bisulfite-induced modification of genomic DNA under conditions whereby unmethylated cytosine is converted to uracil. The bisulfite-modified sequence is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced or can be cloned and sequenced to provide methylation maps of single DNA molecules. See Frommer, M. et al., *Proc. Natl. Acad. Sci.* 89: 1827–1831 (1992).

Similarly, methylation-specific PCR, another widely used assay, can assess the methylation status of CpG dinucleotide sites within a CpG island, independent of the use of methylation-sensitive restriction enzymes. This assay entails the initial modification of DNA by sodium bisulfite or another comparable agent thus converting all unmethylated, but not methylated, cytosines to uracil. Subsequent amplification with primers specific for methylated DNA results in the amplification of DNA consisting of methylated CpG dinucleotides. See Pat. No. 5,786,146; Herman et al., *Proc. Natl. Acad. Sci. USA* 93: 9821–9826 (1996).

These approaches have yielded important information regarding the local methylation control of individual genes. However, current methods have been restricted to analyzing one gene at a time and have not been used to conduct a genome-wide study. As a further step toward a more comprehensive understanding of the underlying mechanisms, it is necessary to perform large-scale or a genome-wide analysis of methylation patterns of DNA in cancer cells.

Accordingly, a need presently exists for technology designed to detect methylation of DNA on a large scale, to identify previously uncharacterized CpG islands associated with gene silencing and to shed light on other, as yet unidentified factors governing aberrant methylation of CpG island loci. Each cancer type may have its own unique methylation pattern that defines its growth rate, tendency to spread, and responsiveness to therapies. By examining a large number of loci in a series of cancers, global methylation profiles can be constructed. Cataloging these molecular patterns could lead to early detection, more accurate diagnosis, and development of better treatment therapies of cancer.

SUMMARY OF THE INVENTION

Accordingly, among the objects of the present invention may be noted the provision of a novel DNA array-based method, differential methylation hybridization (DMH) to detect the presence or absence of hypermethylated nucleic acid sequences in a cell sample. DMH utilizes a set of CpG dinucleotide rich fragments prepared from tumor cells or normal cells to simultaneously screen numerous genomic nucleic acid fragments. The use of DMH provides an accurate and efficient method for the identification of DNA methylation patterns in cancer and thus, DMH has wide-ranging applications in clinical diagnosis and genetic typing of cancer.

An object of the present invention is to provide a process for detecting the presence or absence of methylation of a CpG dinucleotide rich region of a nucleic acid sequence within a genome. A nucleic acid sequence is digested with a enzyme which digests nucleic acid sequences into fragments in which CpG islands are preserved. These fragments containing the CpG islands are then digested with a methylation-sensitive enzyme resulting in a digestion product comprising methylated CpG island loci. The digestion product is amplified and labeled to form amplicons which are used to screen a plurality of nucleic acid fragments affixed to a solid support. The presence or absence of labeled amplicons bound to the plurality of nucleic acid fragments of the screening array is then determined.

It is another object of the present invention to provide a process for identifying methylation patterns in a cancer cell using amplicons generated from cancer and non-cancer cells to screen an array containing genomic fragments.

Another object of the present invention is to provide a screening array comprising a solid support and a plurality of CpG dinucleotide rich fragments affixed to the solid support. The CpG dinucleotide rich fragments are at least about 200 nucleotides in length and contain at least 50% guanine and cytosine.

Yet another object of the present invention is to provide a process for generating a screening array comprising a plurality of nucleic acid fragments containing expressed sequences which includes contacting a nucleic acid sequence with an enzyme which digests the nucleic acid sequences into fragments in which CpG islands are preserved; amplifying and screening the fragments to identify sequences which include expressed sequences and affixing the fragments containing expressed sequences to a solid support. It is another object of the present invention to provide a set of amplicons to be used to probe the nucleic acid fragments affixed on a solid support of the screening array. The amplicons are CpG dinucleotide rich fragments which are derived from digesting a nucleic acid sequence with a restriction enzyme which digests the sequence into fragments in which CpG dinucleotide fragments are preserved. The resulting digestion products are then amplified and used to probe nucleic acid fragments of the screening array.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

FIG. 9A is the initial screening and FIG. 9B is the corresponding subarray. Both FIGS. 9A and 9B are shown with some of the hypermethylated clones later dotted on the subarray dotted with their x- and y-coordinates. PCR products of CpG island tags were dotted onto membranes hybridized first with radiolabeled normal amplicons. The same membranes, or duplicate membranes, were later hybridized with tumor amplicons. Each CpG island tag is represented with two parallel dots in order to differentiate specific hybridization signals from non-specific background signals, which generally appear as scattered single dots. Five to six sets of positive controls were dotted on the four corners of the arrays to serve as orientation markers and for comparison of hybridization signal intensities.

DEFINITIONS AND ABBREVIATIONS

Figure 1:
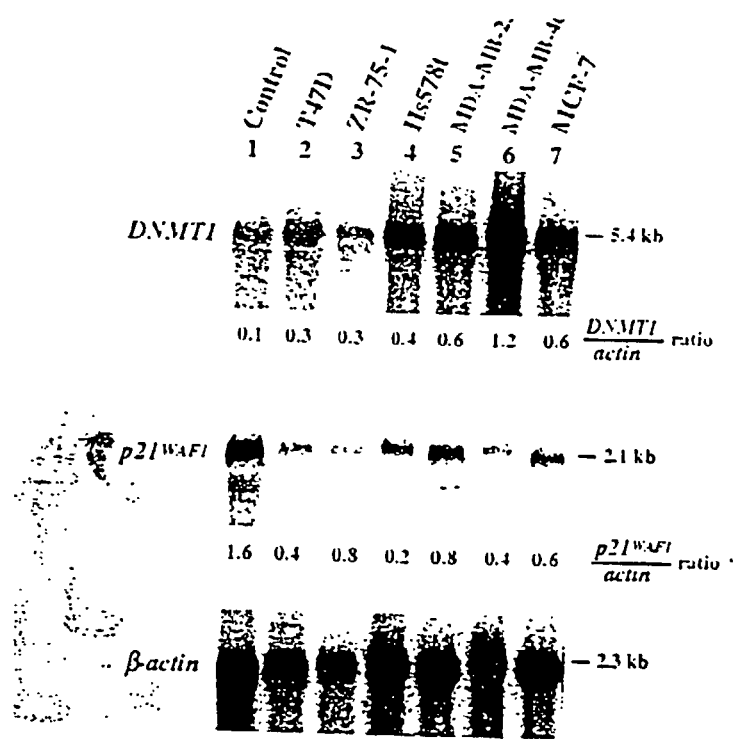
FIG. 1 is a Northern hybridization analysis of DNMT1 and p21$^{WAF1}$ gene expression in breast cancer cell lines. Total RNA (20 Fg) isolated from normal fibroblast (lane 1) and breast cancer cell lines—T47D (lane 2), ZR-75-1 (lane 3), Hs578t (lane 4), MDA-MB-231 (lane 5), MDA-MB-468 (lane 6), and MCF-7 (lane 7) was subjected to Northern analysis. The membrane was probed with DNMT1 (top panel), p21$^{WAF1}$ (middle panel), and b-actin (bottom panel), respectively. The predicted sizes (kb) of the indicated transcripts were calculated using the RNA MW I ladder (Boehringer Mannheim) as a standard. Band intensities were quantified with ImageQuant Software (Molecular Dynamics) and the relative levels of DNMT1 and p21$^{WAF1}$ mRNAs were normalized with the expression level of b-actin in each sample lane.

To facilitate understanding of the invention, a number of terms are defined below:

The nucleotide bases are abbreviated herein as follows: A represents adenine; C represents cytosine; G represents guanine; T represents thymine; U represents uracil.

As used herein, the terms "GC dinucleotide" and "CpG dinucleotide" are used interchangeably.

As used herein, the terms "GC-rich" and "CpG dinucleotide rich" are used interchangeably.

As used herein, the terms "screening" and "probing" are used interchangeably.

A "CpG dinucleotide" is a dinucleotide sequence containing an adjacent guanine and cytosine where the cytosine is located 5' of guanine.

A "CpG dinucleotide rich" nucleic acid fragment may be any nucleic acid fragment in which CpG dinucleotides comprise at least 50% of the nucleic sequence and which have a length of at least 200 base pairs.

A "CpG island" is a CpG dinucleotide rich region where CpG dinucleotides comprise at least 50% of the DNA sequence.

"DMH" is the abbreviation for differential methylation hybridization.

"ECIST" is the abbreviation for Expressed CpG Island Sequence Tags.

"HBC" is the abbreviation for "hypermethylation in breast cancer."

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press as incorporated herein by reference.

DETAILED DESCRIPTION

The present invention provides differential methylation hybridization (DMH) for a high-throughput analysis of DNA methylation. Unlike presently existing methylation analysis methods such as Southern hybridization, bisulfite DNA sequencing and methylation-specific PCR which are restricted to analyzing one gene at a time, DMH utilizes numerous CpG dinucleotide rich genomic fragments specifically designed to allow simultaneous analysis of multiple, preferably hundreds and more preferably, thousands of methylation-associated genes in the genome. As such, the use of DMH provides an accurate and efficient means for the identification of DNA methylation patterns in cells and thus, DMH has wide-ranging applications in clinical diagnosis and genetic typing of cancer.

DMH integrates a high-density, microarray-based screening strategy to detect the presence or absence of methylated CpG dinucleotide genomic fragments. See Schena et al., Science 270: 467–470 (1995). In a preferred embodiment, CpG dinucleotide nucleic acid fragments from a genomic library are generated, amplified and affixed on a solid support to create a CpG dinucleotide rich screening array. Amplicons are generated by digesting DNA from a sample with restriction endonucleases which digest the DNA into fragments but leaves the methylated CpG islands intact. These amplicons are used to probe the CpG dinucleotide rich fragments affixed on the screening array to identify methylation patterns in the CpG dinucleotide rich regions of the DNA sample. Accordingly, DMH may be used to identify hypermethylated sequences in cancer cells by the simultaneous screening of numerous amplified ECIST DNA fragments. Using such technology, it is possible to generate an index set of genes which are commonly methylated in various types of cancer and an index set of genes which are specifically methylated for a particular type of cancer. Thus, DMH can be a useful diagnostic tool for a large scale or a genome-wide screening of methylation of DNA in cancer and may be directly applied in a clinical setting for patient analysis.

The Screening Array

The screening array of the present invention comprises multiple CpG dinucleotide rich fragments affixed to a solid support. These CpG dinucleotide rich fragments affixed to the solid support of the screening array are employed to identify the presence or absence of methylated sites in cells. Further, these CpG dinucleotide fragments may be any nucleic acid fragment in which CpG dinucleotides comprise at least 50% of the nucleic sequence and which have a length of at least 200 base pairs. In a preferred embodiment, the CpG dinucleotide fragments affixed to the solid support of the screening array are selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 and SEQ ID NO: 46.

Preferably, the CpG dinucleotide fragments are derived from DNA clones selected from a genomic library, and more preferably from a genomic library in which the concentration of CpG dinucleotides has been enriched. Examples of such CpG dinucleotide rich genomic libraries are the CGI library, the avian CGI library and the mouse CGI library, each of which is available from the United Kingdom Human Genome Center. In a preferred embodiment, the nucleic acid fragments are derived from DNA clones of the CGI library and are, themselves, CpG islands.

If the nucleic acid fragments are derived from DNA clones of a pre-existing library such as the CGI library, the library is preferably pre-screened with an enzyme to eliminate repetitive sequences. Repetitive sequences are short stretches of DNA dispersed throughout the genome in thousands of copies with no apparent known function which could potentially interfere with the hybridization process. A preferred method utilizes Cot-1 which hybridizes with repetitive sequences such as AluI and KpnI families. DNA clones negative or weakly positive for the Cot-1 hybridization signals are then selected for amplification, i.e., clones positive for Cot-1 DNA are not selected.

The selected CpG dinucleotide nucleic acid fragments are amplified using methods of amplification known in the art. Any nucleic acid specimen can be utilized as the starting nucleic acid template, provided that it contains the specific nucleic acid sequence containing the target DNA sequence i.e., the CpG island. Thus, the amplification process may employ DNA or RNA, wherein DNA or RNA may be double or single stranded. In the event that RNA is to be used as a template, enzymes, and/or conditions optimal for reverse transcribing the template to DNA known to those in the art would be utilized.

Suitable in vitro amplification techniques include but are not limited to, the polymerase chain reaction (PCR) method, transcription-based amplification system (TAS), self-sustained sequence replication system (3SR), ligation amplication reaction (LAR), Qβ RNA replication system and run-off transcription. A preferred method of amplification is PCR amplification which involves an enzymatic chain reaction in which exponential quantities of the target locus (i.e., CpG islands) are produced relative to the number of reaction steps performed. PCR amplification techniques and many variations of PCR are known and well documented. See e.g., Saiki et al., Science 239: 487–491 (1988); U.S. Pat. Nos. 4,682,195, 4,683,202 and 4,800,159, which are incorporated herein by reference.

Typically, the selected DNA clone is denatured, thus forming single strands which are used as templates. One oligonucleotide primer is substantially complementary to the negative (−) strand and another primer is substantially complementary to the positive (+) strand. DNA primers are DNA sequences capable of initiating synthesis of a primer extension product. Primers "substantially complementary" to each strand of the target nucleic acid sequence will hybridize to their respective nucleic acid strands under favorable conditions known to one skilled in the art e.g., pH, salt, cation, temperature. In a preferred embodiment, the primers used in the amplification step are HGMP 3558: 5'

CGG CGG CCT GCA GGT CTG ACC TTA A (SEQ ID NO: 47) and HGMP 3559: 5' AAC GCG TTG GGA GCT CTC CCT TAA (SEQ ID NO: 48).

Annealing the primers to the denatured DNA templates is followed by extension with an enzyme to result in newly synthesized+and−strands containing the target DNA sequence containing the CpG islands. This annealing process consists of the hybridization of the primer to complementary nucleotides of the DNA sequence template in a buffered aqueous solution. The buffer mixture containing the DNA templates and the primers is then heated to a temperature sufficient to separate the two complementary strands of DNA. In a preferred embodiment, the mixture containing the DNA templates and the primers is heated to about 90 to 100° C. from about 1 to 10 minutes, even more preferably from 1 to 4 minutes to allow the DNA templates to denature and form single strands. The mix is next cooled to a temperature sufficient to allow the primers to specifically anneal to sequences flanking the gene or sequence of interest. Preferably, the mixture is cooled to 50 to 60° C., for approximately 1 to 5 minutes. It is understood that the nucleotide sequence of the primer need not be completely complementary to the portion of the DNA template in order to effectively anneal to the DNA template.

A primer extension enzyme is then added which will initiate the primer extension reaction to produce newly synthesized DNA strands. Heat stable enzymes such as pwo, *Thermus aquaticus* or *Thermococcus litoralis* DNA polymerases which eliminate the need to add enzyme after each denaturation cycle may be used as the primer extension enzyme. Other preferred amplification enzymes which may be used include but are not limited to, *Escherichia coli* DNA polymerase I, Klenow fragment of *E. coli* DNA polymerase I, T4 DNA polymerase, T7 DNA polymerase *Thermus aquaticus* (Taq) DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase. The temperature of the reaction mixture is then set to the optimum for the DNA polymerase to allow DNA extension to proceed.

These newly synthesized strands are used as templates in repeated cycles of amplification. Thus, PCR consists of multiple cycles of DNA melting, annealing and extension resulting in an exponential production of the target DNA sequence containing the target CpG islands.

After amplification, methylation-sensitive sites of the amplified products are preferably identified by digestion with a methylation-sensitive restriction enzyme. Examples of such methylation-sensitive enzymes are BstU I, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are used for DMH analysis.

The amplified CpG dinucleotide rich fragments are denatured, transferred to a solid support and immobilized on the solid support using methods known in the art. Such methods that may be used to crosslink the CpG dinucleotide rich fragments to the solid support include but are not limited to UV light, poly-L-lysine treatment and heat. In a preferred embodiment, the CpG dinucleotide rich fragments are denatured, transferred and immobilized using an UV light to crosslink the CpG dinucleotide rich fragments to the solid support. Depending upon the assay, at least 20, preferably at least 100, more preferably at least 500, or even most preferably at least 1,000 amplified CpG dinucleotide rich fragments are transferred to and immobilized on the solid support.

In a preferred embodiment of the invention, the CpG dinucleotide rich fragments affixed to the solid support of the screening array are CpG islands containing expressed sequences. CpG island fragments which contain expressed sequences are referred to herein as Expressed CpG Island Sequence Tags (ECIST). In a preferred embodiment, ECIST fragments contain part of the promoter and the first exon of a gene. Typically, the length of each ECIST fragment is at least 0.3 kb, preferably 0.4 to 0.5 kb, and most preferably 0.4 kb. In a preferred embodiment, the ECIST fragments affixed to the solid support of the screening array are CpG island fragments selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 and SEQ ID NO: 46.

ECIST fragments may be identified after the DNA clone is selected from a genomic library and amplified as described above. ECIST fragments are identified by transferring the amplified CpG dinucleotide rich fragments to membranes and screening the CpG dinucleotide rich fragments with a nucleic acid probe to detect the CpG dinucleotide rich fragments which contain sequences expressed in the sample to be evaluated. The nucleic acid probe used for detection of ECIST fragments may be from any source including breast, colon, ovarian, lung and prostate tissue and may be extracted using a variety of methods known in the art. Further, the nucleic acid probe may be DNA, cDNA, or RNA of the gene, or a fragment of the gene, having at least one of the target sequences described above, or an RNA fragment corresponding to such a cDNA fragment. In a preferred embodiment, the nucleic acid probe used to screen for ECIST fragments is a cDNA probe. A positive hybridization signal of the nucleic acid probe to the amplified CpG dinucleotide rich fragment is indicative of a ECIST fragment.

After screening to identify ECIST fragments, methylation-sensitive sites of the amplified products are preferably identified by digestion with a methylation-sensitive restriction enzyme. Examples of such methylation-sensitive enzymes are BstU I, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are ECIST fragments which are used for DMH analysis. Where the CpG dinucleotide fragments are ECIST fragments, the undigested nucleic acid fragment contains part of the promoter and first exon of the expressed genes.

The ECIST fragments are denatured, transferred to a solid support and immobilized on the solid support using methods known in the art. Such methods that may be used to crosslink the ECIST fragments to the solid support include but are not limited to UV light, poly-L-lysine treatment and heat. In a preferred embodiment, the ECIST fragments are denatured, transferred and immobilized using an UV light to crosslink the ECIST fragments to the solid support. Depending upon the assay, at least 20, preferably at least 100, more preferably at least 500, or even most preferably at least 1,000 amplified ECIST fragments are transferred to and immobilized on the solid support.

The ECIST fragments affixed to the solid support are used to identify the presence or absence of methylated CpG dinucleotide sites in a cell sample. Further, the exon-containing portions of ECIST sequences may be used for measuring levels of the corresponding gene expression in the cell sample being tested.

Accordingly, the present invention is directed to a process for generating a screening array containing expressed gene sequences including:

a. contacting a nucleic acid sequence with an enzyme which digests the nucleic acid sequence into fragments in which CpG islands are preserved;

b. amplifying the fragments to form a plurality of CpG island fragments;

c. screening the plurality of CpG island fragments with a nucleic acid probe to identify CpG island fragments which contain expressed sequences; and d. affixing the CpG island fragments which contain expressed sequences onto a solid support of the screening array.

In addition to the CpG dinucleotide fragments, other known DNA sequences may be placed on the solid support to serve as orientation marks and for normalization of hybridization signal intensities. For example, CpG dinucleotide fragments for ER, WT1, Rb and p16 may be used.

Any solid support to which the CpG dinucleotide rich fragments may be attached may be employed in the present invention. Examples of suitable solid support materials include, but are not limited to, silicates such as glass and silica gel, cellulose and nitrocellulose papers, and nylon membranes. The solid support material may be used in a wide variety of shapes including, but not limited to slides and membranes. Slides provide several functional advantages and thus are a preferred form of solid support. Due to their flat surface, probe and hybridization reagents can be minimized using glass slides. Slides also enable the targeted application of reagents, are easy to keep at a constant temperature, are easy to wash and facilitate the direct visualization of RNA and/or DNA immobilized on the solid support.

A universal or generic DNA array containing these CpG dinucleotide rich fragments can be developed to use as a hybridization template for methylation screening of various types of cancer. Such cancers include but are not limited to breast, prostate, colon, lung, liver and ovarian cancer. However, those skilled in the art will be able to develop screening arrays containing CpG dinucleotide rich fragments specific for particular cancer types.

Preparation of Amplicons

The amplicons of the present invention are amplified nucleic acid fragments derived from a cell sample which are used to probe the CpG dinucleotide rich fragments of the screening array. Generally, amplicons are single or double-stranded amplification products which contain a copy of the target nucleic acid sequence. Amplicons are prepared by isolating and purifying a nucleotide sequence, preferably DNA, from a sample and digesting the isolated and purified nucleotide sequence with a restriction endonuclease which cuts the sequence into fragments but leaves CpG dinucleotide rich regions, i.e., CpG islands intact.

The sample of genomic DNA may be obtained from normal (control) cells, an individual's primary tumors or from clinical specimens containing tumor cells. Cancerous cell types which may be used to prepare the amplicons include but are not limited to breast cancer, ovarian cancer, colon cancer, leukemia, kidney cell cancer, liver cell cancer and lung cancer. Genomic DNA samples can be obtained from any mammalian body fluid, secretion, cell-type or tissue, as well as any cultured cell or tissue. In a preferred embodiment, two sets of amplicons containing methylated CpG dinucleotide sequences are prepared. One set of amplicons is prepared from DNA from non-tumor (control) cells to be used as a reference and a second set of amplicons is prepared from tumor cells.

It is preferred that the restriction enzyme used is an enzyme which has a recognition sequence in regions other than the CpG dinucleotide rich regions of the nucleotide sequence. In a preferred embodiment, the restriction enzyme digests the portions of the nucleotide sequence not containing CpG dinucleotides into fragments having a length of less than 200 base pairs which are then discarded. Examples of appropriate restriction enzymes include but are not limited to MseI, Tsp509I, NlaIII and BfaI. In a more preferred embodiment, the restriction enzyme MseI, whose recognition sequence, TTAA rarely occurs in CpG dinucleotide sites, is used to digest the nucleic acid sequence. Preferably, the endonuclease-restricted, intact CpG islands are nucleotide fragments in which CpG dinucleotides comprise at least 50% of the nucleic acids and are typically between 200 to 2,000 base pairs in length.

The cleaved ends of the endonuclease-restricted, intact CpG islands are then ligated to linker primers and amplified. The endonuclease-restricted CpG islands are preferably amplified according to the procedure outlined above. In a preferred embodiment, unphosphorylated linker primers such as H24 5' AGG CAA CTG TGC TAT CCG AGG GAT (SEQ ID NO:49) and H12 5'TAA TCC CTC GGA (SEQ ID NO:50) are employed in the extension step of PCR amplification.

Because repetitive DNA sequences in the amplified CpG islands may later interfere with the hybridization process, such sequences may optionally be depleted from the ligated DNA using a subtractive hybridization approach. Examples of repetitive sequences are the Alu I and Kpn I families. Various subtractive hybridization techniques are known and well documented in the art. See e.g., Akopyants et al., *Proc. Natl. Acad. Sci. USA* 95:13108–13 (1998); Lee J. H. and Welch D. R., *Int. J. Cancer* 71: 1035–44 (1997); U.S. Pat. Nos. 5,591,575 and 5,589,339. In a preferred embodiment, a subtractive hybridization approach is carried out using Cot-1 in which human Cot-1 DNA containing enriched repetitive sequences is preferably nick translated, biotin-labeled and added to the treated genomic DNA. See Craig et al., *Hum. Genet.*, 100: 472–476 (1997) as incorporated herein by reference The resulting DNA mixture is then purified and denatured, and the biotin labeled repetitive sequences are allowed to hybridize to the complementary repetitive sequences on the genomic DNA. Biotin has a high affinity for avidin; therefore, when streptavidin-magnetic particles are added to the DNA mixture, the repetitive sequence hybrids will attach to the magnetic particles via biotin-streptavidin interaction. The repetitive sequence hybrids are then separated from the CpG islands using a magnetic particle separator. The supernatant containing the CpG islands is removed and purified using methods known in the art.

The resulting amplicons containing methylated and unmethylated CpG islands are purified and digested with appropriate methylation-sensitive restriction enzymes. The methylation-sensitive restriction enzymes will cut their DNA recognition sites when those sites are not methylated but do not cut the DNA site if it is methylated. Thus, unmethylated CpG islands are degraded and methylated CpG islands survive the endonuclease treatment. Examples of such methylation-sensitive enzymes are BstU I, SmaI, SacII, EagI, MspI, HpaII, HhaI and BssHII. In a preferred embodiment, BstU I, whose recognition sequence, CGCG, occurs frequently within CpG islands is used. This methylation-sensitive enzyme is particularly preferred if the CpG dinucleotide fragments immobilized on the screening array are derived from DNA clones selected from the CGI genomic library because approximately 80% of the CGI inserts contain BstU I sites. See Cross et al., Nature Genet., 6: 236–244 (1994).

In a preferred embodiment, only a fraction of the methlyated and unmethylated CpG islands are digested with a methylation-sensitive restriction enzyme. The remaining fraction is not digested with a methylation-sensitive enzyme. As a result, two sets of amplicons are generated to probe the CpG dinucleotide rich screening array: one set of amplicons containing methylated and unmethylated amplicons (e.g., amplicons treated with Mse I, but not BstU I) and a second set of amplicons containing methylated amplicons (e.g., amplicons treated with Mse I and BstU I). The set of amplicons containing methylated and unmethylated CpG islands are preferably used a control in hybridization to determine whether the CpG dinucleotide rich nucleic fragments of the screening array are representative of the repertoire of CpG dinucleotide fragments. The second set of amplicons containing methylated CpG islands are then used to identify methylated CpG island sequences in the cell sample.

The endonuclease restricted amplicons are then amplified, preferably using PCR as is generally described above in connection with the preparation of CpG dinucleotide rich fragments. A relatively low number of amplification cycles is preferably used to prevent the overabundance of remaining repetitive sequences generated by PCR. In a particularly preferred embodiment, the amplicons are subjected to least fifteen and no more than about thirty amplification cycles. In a more preferred embodiment, the amplicons are subjected to approximately fifteen amplification cycles.

The amplicons are then preferably purified and labeled. The term "labeled" is herein used to indicate that there is some method to visualize the CpG dinucleotide fragments hybridized to the amplicons. There are many different labels and methods of labeling known to those of ordinary skill in the art. Moreover, a wide variety of direct and/or indirect means are available to enable visualization of the subject nucleic sequences that have hybridized to the prepared DNA array. Suitable visualizing means include radioisotope labels and non-radioisotope labels such as fluorescence-based detection technologies. Examples of radioisotope labels that can be used include $^{32}$P and $^{33}$P-dCTP and examples of non-radioisotope labels that can be used include Cy3-dUTP and Cy5-dUTP. Further, any labeling techniques known to those in the art could be useful to label the subject nucleic acid sequence in of this invention. Several factors may govern the choice of labeling means, including the effect of the label on the rate of hybridization and binding of the methylated amplicons to the CpG dinucleotide rich screening array, the nature and intensity of the signal generated by the label and the expense and ease in which the label is applied.

In particular, the present invention provides a process for isolating a set of amplicons to identify methylation patterns from a cell sample which includes:

a. contacting nucleic acid sequences with an enzyme which digests the nucleic acid sequences into fragments in which CpG islands are preserved;

b. attaching the cleaved ends of the fragments to linker primers to form linker primer products;

c. contacting the linker primer product with a methylation-sensitive enzyme which digests the linker primer products having unmethylated CpG dinucleotide sequences but not methylated CpG dinucleotide sequences to form a digestion product comprising methylated CpG island loci; and d. amplifying the digestion product to form amplicons.

Screening

The labeled amplicons are used to screen the CpG dinucleotide fragments of the screening array produced using the above methods. Labeled amplicons having a complementary sequence to that of a CpG dinucleotide fragment affixed on the solid support of the screening array will result in a positive hybridization signal. Preferably, the CpG dinucleotide fragments affixed to the screening array are ECIST fragments. If amplicons are used to probe ECIST fragments, positive hybridization signals will also indicate the presence of DNA sequences which are expressed in the cell sample.

In a preferred embodiment, methylated (e.g., MseI/BstU I-pretreated amplicons) amplicons are used to screen the CpG dinucleotide rich fragments of the screening array. Positive hybridization signals indicate the presence of methylated DNA in the cell sample.

In particular, the present invention is directed to a process for determining the presence or absence of methylation of a CpG dinucleotide rich region of a nucleic acid sequence within a genome, the process comprising:

(a) contacting the nucleic acid sequence with an enzyme which digests the nucleic acid sequences into fragments in which CpG islands are preserved;

(b) attaching the fragments to linker primers to form linker primer products;

(c) contacting the linker primer products with a methylation-sensitive enzyme which digests the linker primer products having unmethylated CpG dinucleotide sequences but not methylated CpG dinucleotide sequences to form a digestion product comprising methylated CpG island loci;

(d) amplifying the digestion product to form amplicons;

(e) labeling the amplicons;

(f) contacting the labeled amplicons with a screening array comprising a plurality of nucleic acid fragments affixed to a solid support; and (g) determining the presence or absence of labeled amplicons bound to the plurality of nucleic acid fragments of the screening array.

In a preferred embodiment, the CpG dinucleotide fragments of the screening array are screened using two sets of endonuclease treated amplicons: one set of amplicons which contain methylated and unmethylated CpG islands (e.g., amplicons treated with Mse I, but not BstU I) and a second set of amplicons which contain methylated CpG islands (e.g., amplicons treated with MseI and BstU I). This first set of amplicons containing methylated and unmethylated CpG islands is preferably used as a control in hybridization to determine whether the amplified products are representative of the repertoire of CpG dinucleotide rich fragments. Preferably, the first set of amplicons containing methylated and unmethylated amplicons are amplicons treated with Mse I. The first set of amplicons is completely removed and the screening array is then rehybridized using the second set of amplicons containing methylated CpG islands. Alternatively, the second set of amplicons containing methylated CpG islands is used to screen a second screening array containing CpG dinucleotide fragments which are identical to the CpG dinucleotide fragments of the screening array probed with the first set of amplicons. In a preferred embodiment, the second set of amplicons contain Mse I/BstU I-pretreated amplicons. Positive hybridization signals resulting from the second hybridization using amplicons containing methylated CpG islands indicate the presence of methylated CpG island sequences in the cell sample being tested. Further, positive hybridization signals using both sets of amplicons (e.g., Mse I treated amplicons and Mse I/BstU I amplicons) indicate the presence of aberrently methylated DNA in the cell sample.

Accordingly, the present invention provides a process for determining the presence or absence of aberrently methylated DNA in a cell sample, said process comprising:

a) preparing a first set of amplicons comprising (i) contacting a nucleic acid sequence with an enzyme which digests the nucleic acid sequences fragments in which CpG islands are preserved to form a digestion product comprising methylated and unmethylated CpG island loci; (ii) attaching the digestion product to linker primers to form linker primer products; (iii) amplifying the linker primer products to form amplicons; (iv) labeling the amplicons;

b) preparing a second set of amplicons comprising (i) contacting nucleic acid sequences with an enzyme which digests the nucleic acid sequences into fragments in which CpG islands are preserved; (ii) attaching the fragments to linker primers to form linker primer products; (iii) contacting the linker primer products with a methylation-sensitive enzyme which digests the linker primer products having unmethylated CpG dinucleotide sequences but not methylated CpG dinucleotide sequences to form a second digestion product comprising methylated CpG island loci; (iv) amplifying the second digestion product to form amplicons; (v) labeling the amplicons;

c) contacting the first set of amplicons with a first screening array comprising a plurality of nucleic acid fragments affixed to a solid support and determining the presence or absence of labeled amplicons bound to the plurality of nucleic acid fragments of the first screening array;

d) contacting the second set of amplicons with a second screening array which comprises a plurality of nucleic acid fragments affixed to a solid support wherein the plurality of nucleic acid fragments of the second screening array are identical to the plurality of nucleic acid fragments of the first screening array and determining the presence or absence of labeled amplicons bound to the plurality of nucleic acid fragments of the second screening array; and e) observing whether the presence or absence of the first set of amplicons bound to the nucleic acid fragments of the first screening array is the same as the presence or absence of the second set of amplicons bound to the nucleic acid fragments of the second screening array.

In another preferred embodiment, the screening array is probed using two sets of methylated amplicons. The first set of methylated amplicons is prepared from a non-cancer (control) cell to be used as a reference and the second set of methylated amplicons is prepared from a cancer cell. The CpG dinucleotide fragments of the screening array are first screened using amplicons containing methylated CpG islands prepared from a non-cancer cell. Preferably, Mse I/BstU I treated amplicons from a non-cancer cell will be used in this first hybridization. The first set of methylated amplicons is completely removed and the screening array is then rehybridized using the second set of amplicons containing methylated CpG islands prepared from a cancer cell. Preferably, Mse I/BstU I treated amplicons from a tumor cell will be employed in this second screening. Alternatively, the second set of amplicons are used to screen a second screening array containing CpG dinucleotide fragments which are identical to the CpG dinucleotide fragments of the screening array screened with the first set of methylated amplicons prepared from non-tumor cells. The difference in the hybridization signal intensities using the second set of methylated amplicons from a cancer cell as compared to the intensities of the hybridization signals obtained using the first set of methylated amplicons from a non-cancer (control) cell reflects the aberrant methylation patterns of the corresponding sequences in the cancer cell DNA.

In particular, the present invention is directed to a process for identifying methylation patterns in DNA from a cancer cell including:

a. isolating a first set of amplicons comprising (i) contacting nucleic acid sequences derived from a cancer cell with an enzyme which digests the nucleic acid sequences into fragments in which CpG islands are preserved; (ii) attaching the fragments to linker primers to form linker primer products; (iii) contacting the fragments with a methylation-sensitive enzyme which digests the fragments having unmethylated CpG dinucleotide sequences but not methylated CpG dinucleotide sequences to form a digestion product comprising methylated CpG island loci; (iv) amplifying the digestion product to form amplicons; and (v) labeling the amplicons;

b. isolating a second set of amplicons comprising repeating (i) through (v) of step (a) wherein the nucleic acid sequences of (i) are nucleic acid sequences derived from a non-cancer cell;

c. contacting the first set of amplicons with a first screening array comprising a plurality of nucleic acid fragments affixed to a solid support and determining the presence or absence of labeled amplicons bound to the plurality of nucleic acid fragments of the screening array;

d. contacting the second set of amplicons with a second screening array comprising a plurality of nucleic acid fragments affixed to a solid support wherein said plurality of nucleic acid fragments of the second screening array are identical to the plurality of nucleic acid fragments of the first screening array and determining the presence or absence of labeled amplicons bound to the plurality of nucleic acid fragments of the second screening array; and e. observing whether the presence or absence of the first set of amplicons bound to the plurality of nucleic acid fragments of the first screening array is the same as the presence or absence of the second set of amplicons bound to the plurality of the nucleic acid fragments of the second screening array.

Preferably, gene silencing associated with DNA methylation can be confirmed by rescreening the same screening array with cDNA derived from the cancer samples using methods known in the art.

Experimental results utilizing the present DHM methods suggest that alterations of cell methylation patterns is related to tumor growth in cancer development. Specifically, the present DMH methods have been used to identify hypermethylated CpG island sites which may act as markers indicating whether a patient has cancer. These sites were identified using tumor cells from breast cancer patients. The alteration of the methylation pattern in CpG dinucleotides may be a key, and a common event, in the development of neoplasia. Aside from effect of DNA-MTase on methylation, the present experiments suggest that additional factors such as pre-existing methylation of CpG dinucleotides may account for de novo methylation in cancer cell lines.

Without being bound by any theory, a mechanism may exist whereby methylated CpG islands could progressively accumulate during tumor development; therefore, pre-existing methylation within a CpG island locus may promote subsequent de novo methylation in cancer cells. As a result of CpG island hypermethylation, critical tumor suppressor genes may become silenced, leading to some cells with growth advantage. The results of the experiments discussed in the following examples offer an alternative explanation for the underlying mechanisms in direct contrast to the random nature of the de novo DNA methylase activities previously proposed in transformed cells.

Further, differential methylation patterns in various clinical specimens may reflect different stages or types of cancer. Thus, a determination of the methylation patterns in tumor cells would allow for the identification of gene markers indicative of cancer. Hence, the present DMH methods have broad utility for identifying differentially methylated CpG island sites in a genome; for mapping hypermethylated DNA sites which are related to disease development; for understanding the role of DNA methylation in normal cell genomic DNA imprinting, differentiation, and development; for understanding the role of DNA methylation in tumorigenesis; and for diagnosing and monitoring the prognosis of disease.

The following examples illustrate the invention, but are not to be taken as limiting the various aspects of the invention so illustrated.

EXAMPLE 1

Materials and Methods

Cell culture and tissue sample preparations. The T47D, ZR-75-1, Hs578t, and MDA-MB-468 breast cancer cell lines were acquired from the American Type Culture Collection (Rockville, Md.). The MDA-MB-231 and MCF-7 cell lines were obtained from Dr. Wade V. Welshons at the University of Missouri School of Veterinary Medicine (Columbia, Mo.). T47D and ZR-75-1 were maintained in RPMI 1640 media with 10% fetal bovine serum, while the remaining cell lines were maintained in Earle's Modified Eagle's Medium with 10% fetal bovine serum. Breast tumor and adjacent, non-neoplastic tissue (used as a normal control) were obtained from patients undergoing mastectomies at the Ellis Fischel Cancer Center (Columbia, Mo.). Total RNA and genomic DNA from samples were isolated using the RNeasy Total RNA Kit™ (Qiagen) and QIAamp Tissue Kit™, respectively.

Northern hybridization. Twenty mg of total RNA from breast cancer cell lines and a normal control fibroblast sample were electrophoresed on a 1.4% agarose gel in the presence of 2.2 mM formaldehyde and transferred to a nylon membrane. cDNA probes were prepared from cells known to express DNMT1 and p21$^{WAF1}$ by reverse transcription-PCR. A 192-bp product was generated for DNMT1 using primers 5' ATC TAG CTG CCA AAC GGA G (sense strand) and 5' CAC TGA ATG CAC TTG GGA GG (antisense strand). A 206-bp product was generated for p21$^{WAF1}$ using primers 5' AAC TAG GCG GTT GAA TGA GAG GTT (sense strand) and 5' GTG ACA GCG ATG GGA AGG AG (antisense strand). The resulting PCR products were isolated and $^{32}$P-labeled using the Multiprime DNA labeling system (Amersham). The Northern membrane was hybridized with radiolabeled DNMT1 and p21$^{WAF1}$ cDNA probes, respectively. Hybridization was performed in 8 ml Hybrisol I (Oncor) at 42° C. overnight. Washing was performed once for 20 min in 0.1% SDS—0.5×SSC (1×SSC is 0.15 M NaCl plus 0.015 M sodium citrate, pH 7.0) and twice for 20 min each in 0.1% SDS—0.2×SSC at 65° C. The same membrane was also hybridized with a $^{32}$P-labeled b-actin cDNA (1.1-kb) probe to determine the amount of RNA loaded. The hybridized membrane was subjected to phosphorimage analysis with a Molecular Dynamics PhosphorImager, and band intensities were quantified with ImageQuant Software (Molecular Dynamics). The levels of DNMT1 and p21$^{WAF1}$ mRNAs were normalized with the level of b-actin mRNA in the respective sample lanes.

Amplicon generation. Approximately 2 mg of genomic DNA from breast cancer cell lines or normal breast tissue were restricted to completion with 10 units of Mse I per mg DNA following the conditions recommended by the supplier (New England Biolabs). The digests were purified, and mixed with 0.5 nmol of unphosphorylated linkers H-24 and H-12 in a DNA ligase buffer (New England Biolabs). The oligonucleotide sequences were as follows: H-24: 5' AGG CAA CTG TGC TAT CCG AGG GAT and H-12: 5' TAA TCC CTC GGA. Oligonucleotides were annealed by cooling the mixture gradually from 50° to 25° C. and then ligated to the cleaved ends of the DNA fragments by incubation with 400 units of T4 DNA ligase (New England Biolabs) at 16° C. Repetitive DNA sequences were depleted from the ligated DNA using a subtraction hybridization protocol described by Craig et al. Briefly, human Cot-1 DNA (20 mg; Gibco/BRL) containing enriched repetitive sequences was biotin-labeled using the Nick Translation Kit (Gibco/BRL) and added to the treated genomic DNA. The DNA mixture was purified and dried under vacuum. The dried mixture was redissolved in 10 ml of 6×SSC and 0.1% SDS, denatured by boiling for 10 min, and hybridized at 65° C. overnight. One hundred ml (1 mg) of streptavidin-magnetic particles were added to the hybridization mixture and incubated at room temperature for 30 min. Streptavidin-magnetic particles were prepared according to the manufacturer's instructions (Boehringer Mannheim). Tubes were applied to a magnetic particle separator (Boehringer Mannheim) and the supernatant was aspirated. This supernatant was incubated again at room temperature for 30 min with freshly prepared streptavidin-magnetic particle solution. After the incubation, the second supernatant was removed and DNA was purified using a QIAquick kit (Qiagen). Half of the resulting DNA was digested with the methylation-sensitive endonuclease BstU I (New England Biolabs) following the conditions recommended by the supplier. PCR reactions were performed with the pretreated DNAs (Mse I or Mse I/BstU I) (500 ng) in a 100 ml volume, containing 0.4 mM T-24 primer, 2 units Deep Vent (exo-) DNA polymerase (New England Biolabs), 5% (v/v) dimethyl sulfoxide, and 200 mM dNTPs in a buffer provided by the supplier. The tubes were incubated for 3 min at 72° C. to fill in 5' protruding ends of ligated linkers and subjected to 15 cycles of amplification consisting of 1 min denaturation at 95° C. and 3 min annealing and extension at 72° C. in a PTC-100 thermocycler (MJ Research). The final extension was lengthened to 10 min. The use of low amplification cycles is essential to prevent overabundance of leftover repetitive sequences generated by PCR. The amplified products, designated as "Mse I-pretreated amplicons" or "Mse I/BstU I-pretreated amplicons," were purified using the QIAquick kit, and 50 ng of the DNA were $^{32}$P-labeled using the random primer labeling system as described above.

Differential methylation hybridization. Approximately 3,000 clones derived from the CGI genomic library were prescreened with $^{32}$P-labeled Cot-1 DNA. Clones negative or weakly positive for the Cot-1 hybridization signals were picked and placed into 96-well PCR microplates. A fraction of each colony was transferred to a well of separate 96-well culture chambers for later use. Insert from each clone was amplified in a total volume of 20 ml per tube following the conditions described earlier. Thirty cycles of amplification were performed with denaturing for 1 min at 94° C., annealing for 1 min at 55° C., and extension for 3 min at 72° C. The primers used for amplification were HGMP 3558: 5° CGG CCG CCT GCA GGT CTG ACC TTA A (SEQ ID NO: 47) and HGMP 3559: 5' AAC GCG TTG GGA GCT CTC CCT TAA (SEQ ID NO: 48). After PCR, 1 ml of the amplified products was digested with the methylation-sensitive BstU I, and the digests were size fractionated on 1% agarose gels. Inserts (0.2 to 1.5-kb) of the tested CGI clones containing multiple BstU I sites (based on the digestion patterns) were selected for further analysis. The remaining DNA was denatured at 95° C. for 5 min, 2 ml of tracking dye (bromophenol blue) was added to each tube and the DNA was transferred to nylon membranes using a 96-pin MULTI-PRINT™ replicator (V & P Scientific). Each PCR sample was dotted in duplicate, and the position of each dot in the array was marked by the tracking dye. Each pin transfers an approximately 0.4 ml-hanging drop (about 40 ng DNA) onto a membrane. An alignment device (LIBRARY COPIER™; V&P Scientific) was used in conjunction with the replicator to convert three 96-well PCR samples in duplicate into one recipient of 276 dots on a 10×12-cm nylon membrane.

Additionally, 3 positive controls were dotted in quadruplicate on the corners (the top and bottom three rows of the first and last columns) of array to serve as orientation marks and for normalization of hybridization signal intensities of dotted genomic fragments. Membranes were first hybridized with 32p-labeled Mse I-pretreated amplicons overnight at 65° C. in 10 ml of High Efficiency Hybridization solution (Molecular Research, Inc.). Washing was performed once for 20 min in 0.1% SDS—0.5×SSC (1×SSC is 0.15 M NaCl plus 0.015 M sodium citrate, pH 7.0) and twice for 20 min each in 0.1% SDS—0.2×SSC at 65° to 75° C. Autoradiography and analysis were completed using the Molecular Dynamics PhosphorImager and the ImageQuant Software as described earlier. Probes were completely stripped, and the same membranes were rehybridized with $^{32}$P-labeled Mse I/BstU I-pretreated amplicons. Each hybridization experiment was independently performed twice using duplicate membranes.

DNA Sequencing. Plasmid DNA was prepared from positive CGI clones and sequenced using the DyeDeoxy Terminator Cycle Sequencing kit and the automated ABI PRISM 377 sequencer. The nucleotide sequence data were compared to GenBank using the BLAST program.

Methylation Analysis by Southern Hybridization. Genomic DNA (10 mg) from breast cancer cell lines or breast specimens was digested to completion with Mse I or Mse I/BstU I. The restriction products were separated on 1.0% agarose gels and transferred to nylon membranes. Portions of CGI clone inserts were PCR-amplified as probes for Southern hybridization. Amplified products were designed to be ~200 to 300-bp in length and contain no BstU I sites. Hybridization was conducted in 8 to 10 ml of High Efficiency Hybridization solution for overnight at 65–70° C. Post-hybridization washing was carried out as described above. Southern blots were subjected to phosphorimage analysis, and band intensities were quantified with the ImageQuant software.

EXAMPLE 2

Expression of DNMT1 and p21$^{WAF1}$ Genes in Breast Cancer Cells

Human cancer cells have increased DNA-MTase activities known to promote CpG island hypermethylation during tumor progression. See Vertino et al., *Mol. Cell Biol.*, 16:4555–4565 (1996); Wu et al., *Cancer Res.*, 56: 616–622 (1996); Belinsky et al., *Proc. Natl. Acad. Sci. USA*, 93: 4045–4050 (1996). Since DNMT1 is primarily responsible for DNA-MTase synthesis, we determined its mRNA levels in breast cancer cell lines T47D, ZR-75-1, Hs578t, MDA-MB-231, MDA-MB-468, and MCF-7.

RNA from breast cancer cell lines T47D, ZR-75-1, Hs578t, MDA-MB-231, MDA-MB-468, and MCF-7 were isolated and prepared for Northern analysis using the methods and materials provided in Example 1. cDNA probes for DNMT1 and p21$^{WAF1}$ were also prepared using the methods and materials described in Example 1. Northern analysis showed 3- to 12-fold higher levels of the 5.4-kb DNMT1 mRNA in these cell lines compared with a normal control sample (FIG. 1, upper panel). These results are consistent with a previous study that showed both increases of DNMT1 mRNA levels and the resulting elevation of DNA-MTase enzyme activities in the same cell lines.

It has also been recently shown that the p21 protein negatively regulates targeting of DNA-MTase to the replication-associated protein PCNA. It has been proposed that the presence of p21 prevents DNA-MTase access to replicating DNA, thereby impeding hypermethylation in normal cells, while loss or decreased expression of p21 in tumor cells may facilitate aberrant methylation. Therefore, the expression of the 2.1-kb p21$^{WAF1}$ transcript, the gene encoding p21 in these breast cancer cells, was detected in the cell lines with levels 2- to 8-fold lower than the normal control sample (FIG. 1, middle panel). This result, together with the DNMT1 finding, suggests that these breast cancer cell lines possess an increased capacity to aberrantly methylate their genomes.

EXAMPLE 3

Methylation Profiling of CpG Islands in Human Breast Cancer Cells by Differential Methylation Hybridization (DMH)

Figure 2:
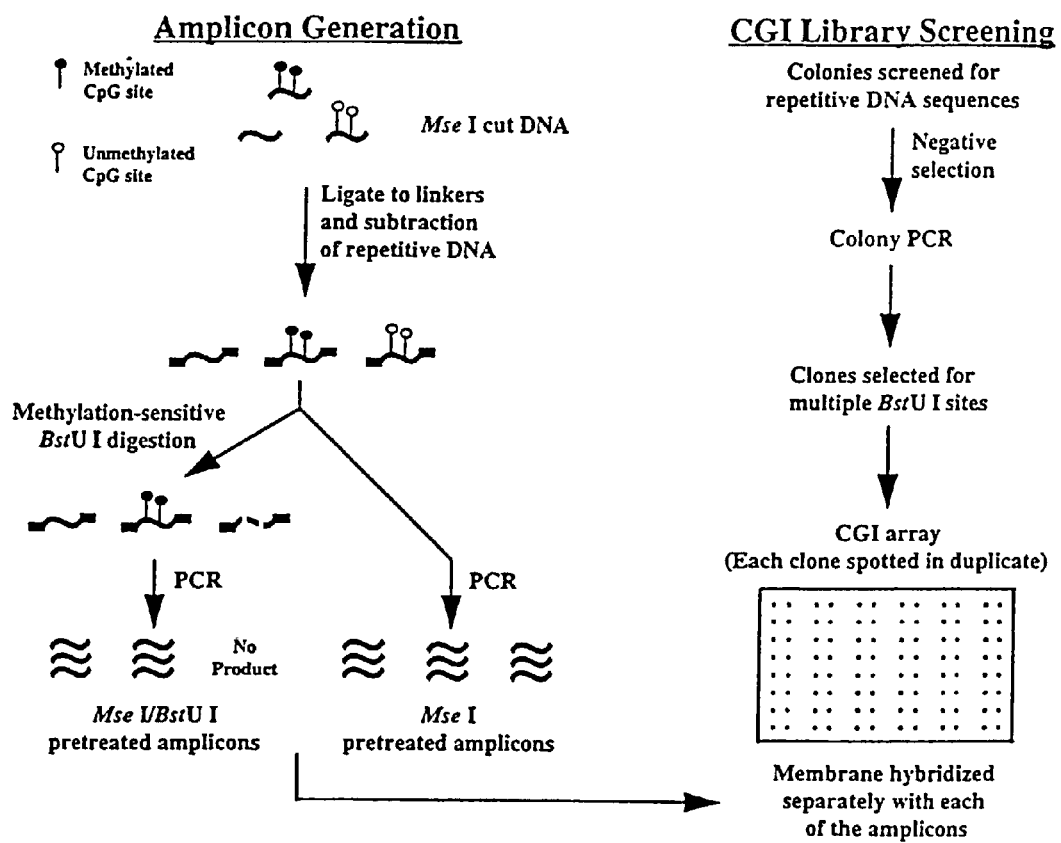
FIG. 2 is a schematic flowchart for differential methylation hybridization. The diagram illustrates the preparation of amplicons used as hybridization probes and selection of CpG island genomic clones gridded on high-density arrays.

DMH was utilized to determine the extent of CpG island sequences undergoing de novo methylation in the 6 cancer cell lines described above in Example 2 (FIG. 2). Genomic DNA from breast cancer cells (T47D, ZR-75-1, Hs578t and MDA-MB-468) was used to prepare amplicons as described above in the Materials and Methods provided in Example 1. DNA from normal breast tissue was similarly digested and used as a control. The cleaved ends of the CpG dinucleotide rich fragments were ligated to linkers and repetitive sequences such as the Alu I and Kpn I families were removed from the digests using a Cot-1 subtractive hybridization approach (see Materials and Methods).

Figure 3:
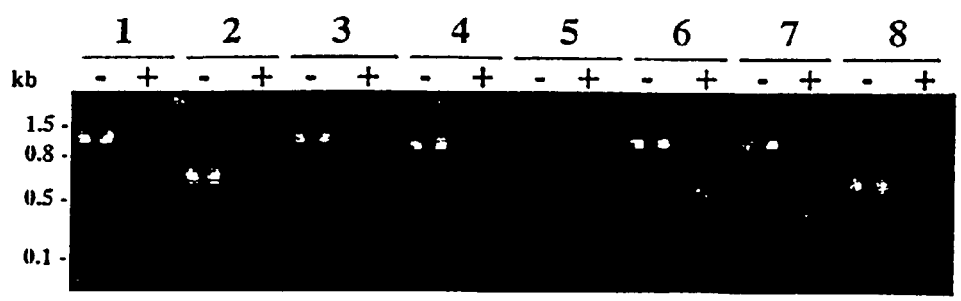
FIG. 3 is BstU I analysis of CpG island clones. Inserts from each clone was amplified by colony PCR and digested with BstU I. The digested (+) and undigested (−) insert DNA samples were separated on 1.5% agarose gels and stained with ethidium bromide. Based on the sizes of the digested fragments, clones containing more than or equal to two BstU I sites were further selected for analysis by differential methylation hybridization. Molecular weight markers (100-bp ladder; Promega) are shown at left.

Half of the subtracted DNA was further treated with methylation-sensitive endonuclease BstU I and both BstU I-digested and undigested, control DNAs were used as templates for linker-PCR (see Material and Methods). Genomic fragments containing unmethylated BstU I sites were cut and could not be amplified in the treated samples, whereas the same fragments were amplified in the undigested, control samples. Some fragments containing methylated BstU I sites in the cells were protected from the digestion and were amplified by linker-PCR. The PCR products designated as "Mse I-pretreated amplicons" or "Mse I/BstU I-pretreated amplicons" were used as probes for screening hypermethylated sequences. CpG island clones were preselected from the CGI library to contain multiple BstU I sites (FIG. 3), and their amplified insert DNA (0.2 to 1.5-kb) was gridded on high-density arrays as described in the Materials and Methods of Example 1.

Results of DMH Analysis

Figure 4:
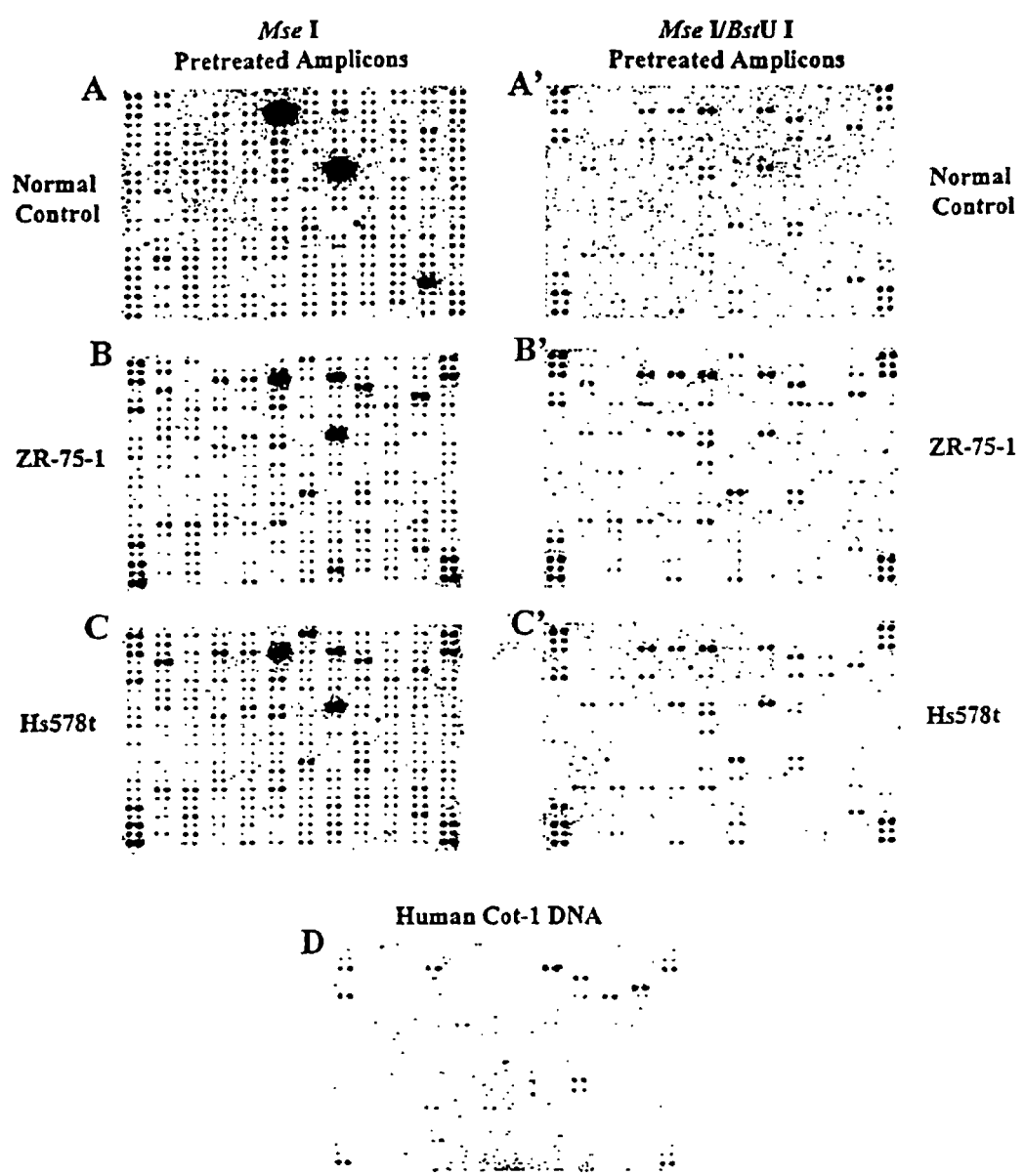
FIG. 4 show representative results of differential methylation hybridization. PCR products of CpG island clones were dotted onto membranes in duplicate and hybridized first with $^{32}$P-labeled Mse I-pretreated amplicons as shown here for a normal breast sample (control), ZR-75-1, and Hs578t breast cancer cell lines (panels A, B, and C). The same membranes were later hybridized with $^{32}$P-labeled Mse I/BstU I-pretreated amplicons (panels A', B' and C'). Panel D: the membrane was hybridized with a repetitive DNA probe, human Cot-1 DNA (Gibco/BRL). Three positive control DNA samples were dotted in quadruplicate on the four corners of array to serve as orientation marks and for comparison of hybridization signal intensities.

FIG. 4 shows the representative results of 276 CpG island loci analyzed by DMH. Various degrees of hybridization signals observed could be attributed to different sizes of amplified products. Mse I-pretreated amplicons were expected to hybridize the matching Mse I-restricted CpG island sequences on the membranes; the hybridization signals, however, were detected in approximately 86% of these island loci (panels A, B, and C). The unhybridized loci could be derived from the Y chromosome due to the fact that this CGI library was originally constructed using male DNA, whereas the amplicons were prepared from female cells. Excluding the unhybridized loci (panel A) and the 14 Cot-1 positive loci (panel D), the Mse I/BstU I-pretreated amplicons derived from a normal breast tissue sample detected positive hybridization signals in 9.7% (23 of 237 loci) of the tested CpG island sequences (panel A'). The positive signals represent methylated BstU I sites located within these CpG island loci, some of which could be derived from the transcriptionally inactivated X chromosome or "imprinted genes." This low percentage is consistent with the notion that the majority of CpG islands are ummethylated in normal cells. A few prominent hybridization signals were observed on the filter hybridized with Mse I-pretreated amplicons (panel A); the intensity of these signals, however, was decreased on the filter hybridized with Mse I/BstU I-pretreated amplicons (panel A'). This may be attributed to the presence of some abundant sequences (e.g., ribosomal DNA or Cot-1 related sequences) known to be methylated in the normal genome.

Figure 5:
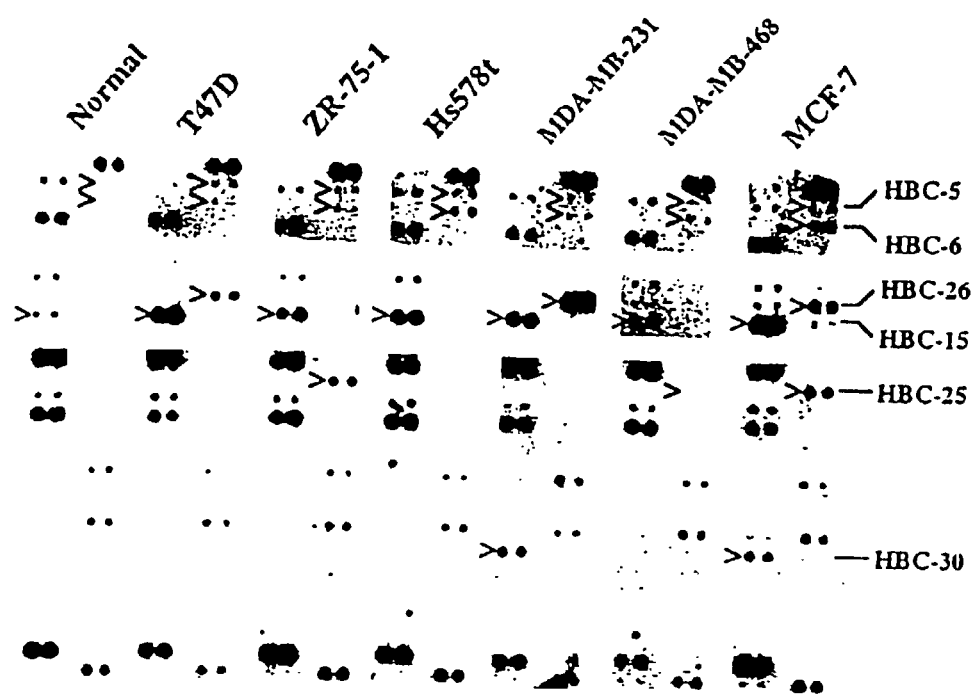
FIG. 5 represents identification of hypermethylated CpG island loci by differential methylation hybridization. PCR products of CpG island clones were dotted onto membranes in duplicate and probed with the Mse I/BstU I-pretreated amplicons for the normal control and breast cancer cell lines as indicated. Probes were prepared as described in the text. Clones shown at right (also marked by >) containing hypermethylated BstU I sites were identified on the autoradiogram showing greater hybridization signal intensities of dots hybridized with probes prepared from the breast cancer cell lines than the same dots probed with the normal breast control.

An increased number of hybridization signals were detected in the CpG island arrays hybridized with the Mse I/BstU I amplicons derived from the 6 breast cancer cell lines. Representative results were shown for cell lines ZR-75-1 and Hs578t (panels B, B', C, and C'). Methylated BstU I sites were observed in 15.0% of these tested loci in Hs578t, 15.6% in T47D, 18.0% in MDA-MB-468, 19.4% in ZR-75-1, 22.7% in MDA-MB-231, and 23.6% in MCF-7 cells, respectively. Although hypermethylation was extensive relative to the normal breast sample, the overall levels varied among these cell lines. Methylation pattern analysis led to the identification of hypermethylated CpG island loci present in these cell lines relative to the normal control; some loci appeared to be methylated in all 6 cell lines, whereas others were sporadically methylated in only a few cell lines (FIG. 5).

Nucleotide Sequencing of Hypermethylated CpG Island Loci

Thirty-four positive CpG island loci selected from the 276 CpG island array and from other DMH screenings were further characterized by nucleotide sequencing. Inserts of these CGI clones were sequenced and internal BstU I sites were verified. The sequence data were used to search for known sequences in the GenBank database. Thirty of these loci are listed in Table 1. (Four other loci not listed here were false-positive findings; their hypermethylation status in breast cancer cells was not confirmed by subsequent Southern analysis.) Nine of the 30 clones contained sequences identical to the known expressed sequences of HPK1, DCIS1, Potassium channel protein, PAX2, PAX7, GALNR2, EST03867, ESTAA827755, and EST88248. Six clones matched existing CpG island sequence tags.

EXAMPLE 4

Figure 6:
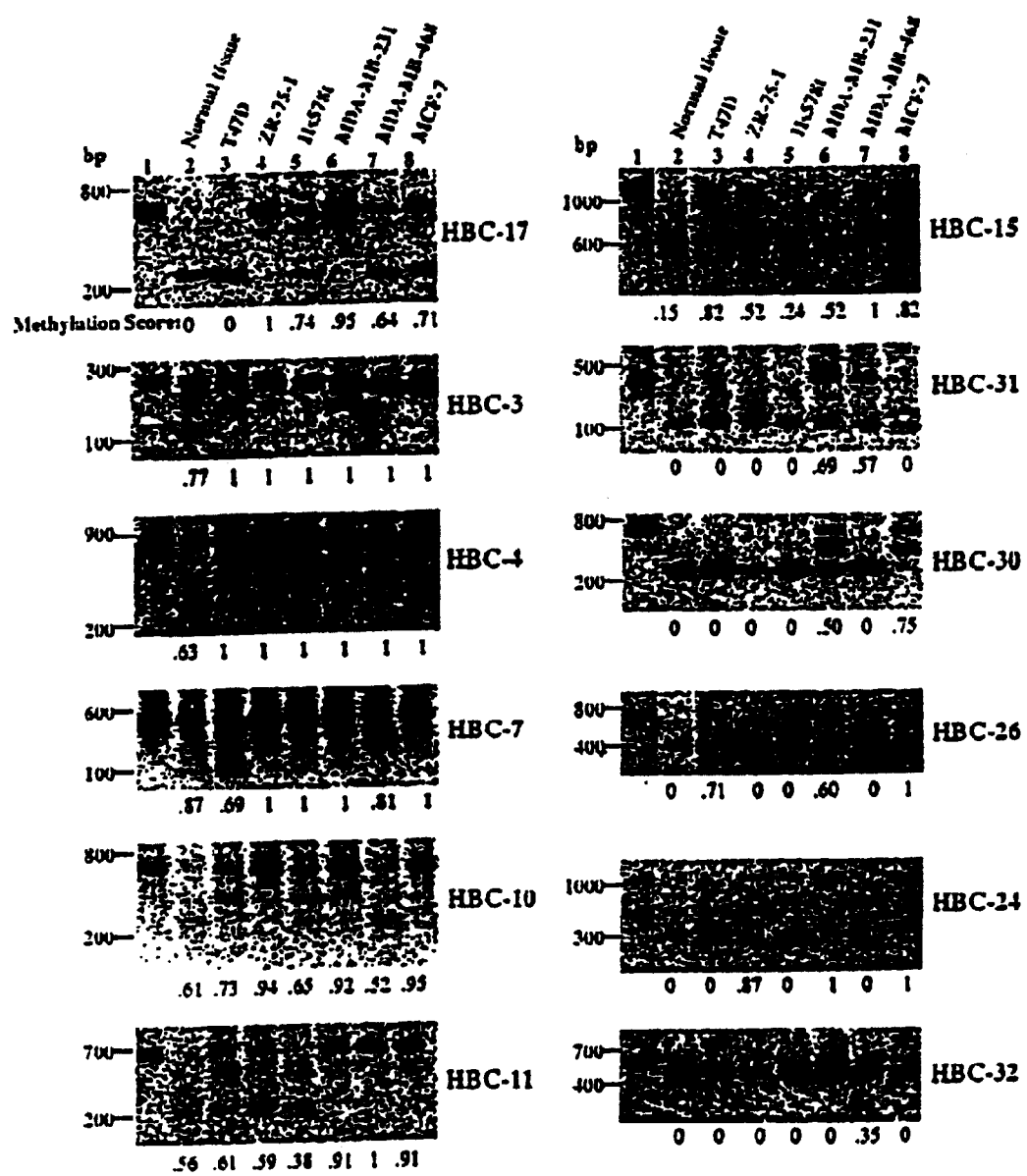
FIG. 6 show representative results of methylation analysis by Southern hybridization. Genomic DNA (10 mg) from a normal breast tissue sample (lane 2) and breast cancer cell lines—T46D (lane 3), ZR-75-1 (lane 4), Hs578t (lane 5), MDA-MB231 (lane 6), MDA-MB-468 (lane 7), and MCF-7 (lane 8) were treated consecutively with Mse I and methylation sensitive BstU I, and subjected to Southern hybridization. Lane 1 contains control DNA digested with Mse I only. The digests were hybridized with genomic fragments (200–300-bp) derived from CpG island clones shown at right. Molecular weight markers (100-bp ladder; Promega) are shown at left. Percent of methylation was calculated as the intensity of the methylation band relative to the combined intensities of all bands. Percent of incomplete methylation was similarly calculated. The methylation score shown at the bottom of each lane was the sum total of the percent of complete methylation multiplied by 0.5.

Profiling Methylation Patterns of CpG Island Loci in Breast Cancer Cells by Southern Hybridization The methylation status of CpG island loci detected in the cancer cell lines was independently confirmed by Southern analysis (FIG. 6). Hybridization probes were generated from the cloned inserts by PCR. Amplified products were designed to be ~200 to 300-bp in length and contain no BstU I sites. For example, the probe for HBC ("hypermethylation in breast cancer")-17 detected a 750-bp fragment in the Mse I-digested, control DNA lane (top left panel, lane 1). The same or similar-sized fragments were detected in the Mse I/BstU I double-digested DNA samples of ZR-75-1, Hs578t, MDA-MB-231, MDA-MB-468, and MCF-7 (lanes 4–8). The presence of this fragment was a result of all the BstU I sites within HBC-17 being insensitive to restriction and, therefore, methylated in these cells. A 300-bp fragment was present in the T47D DNA sample (lane 3). This band was shown in the digested normal, control DNA (lane 2), suggesting all the tested sites were unmethylated in the cells and digested by BstU I to give a 300-bp fragment. The unmethylated fragment was also present in MDA-MB-468 and MCF-7 cells (lanes 7 and 8). Partially methylated fragments (400 and 600-bp) were identified in Hs578t or MDA-MB-231 cells, which can be attributed to a portion of the tested BstU I sites being methylated in HBC-17.

Because it was not possible to measure the degrees of methylation at each tested site based on this Southern analysis, a semiquantitative approach was developed for these samples. First, percent of complete methylation was calculated as the densitometric intensity of the 750-bp fragment relative to the combined intensities of all fragments from each lane. Percent of incomplete methylation (i.e., the 400 and 600-bp fragments) and unmethylation (i.e., the 300-bp fragment) was similarly calculated. Each fraction was further assigned a value, with complete methylation being 1, incomplete methylation 0.5, and unmethylation 0. The methylation score for each sample was the sum total of the percent of complete methylation multiplied by 1 plus the percent of incomplete methylation multiplied by 0.5. The scores derived using this method were in agreement with the results based on a visual comparison of band intensities for each sample lane. This approach was applied for the rest of the CpG island loci. Additional examples of Southern hybridization and the resulting methylation scores are shown in FIG. 6. To ensure a complete methylation-sensitive restriction of the cell line DNA samples, membranes were rehybridized with a negative control probe, 7-120, whose corresponding BstU I sites were known to be unmethylated in the cell line DNA as well as in a few normal breast DNA samples (data not shown).

Figure 7:
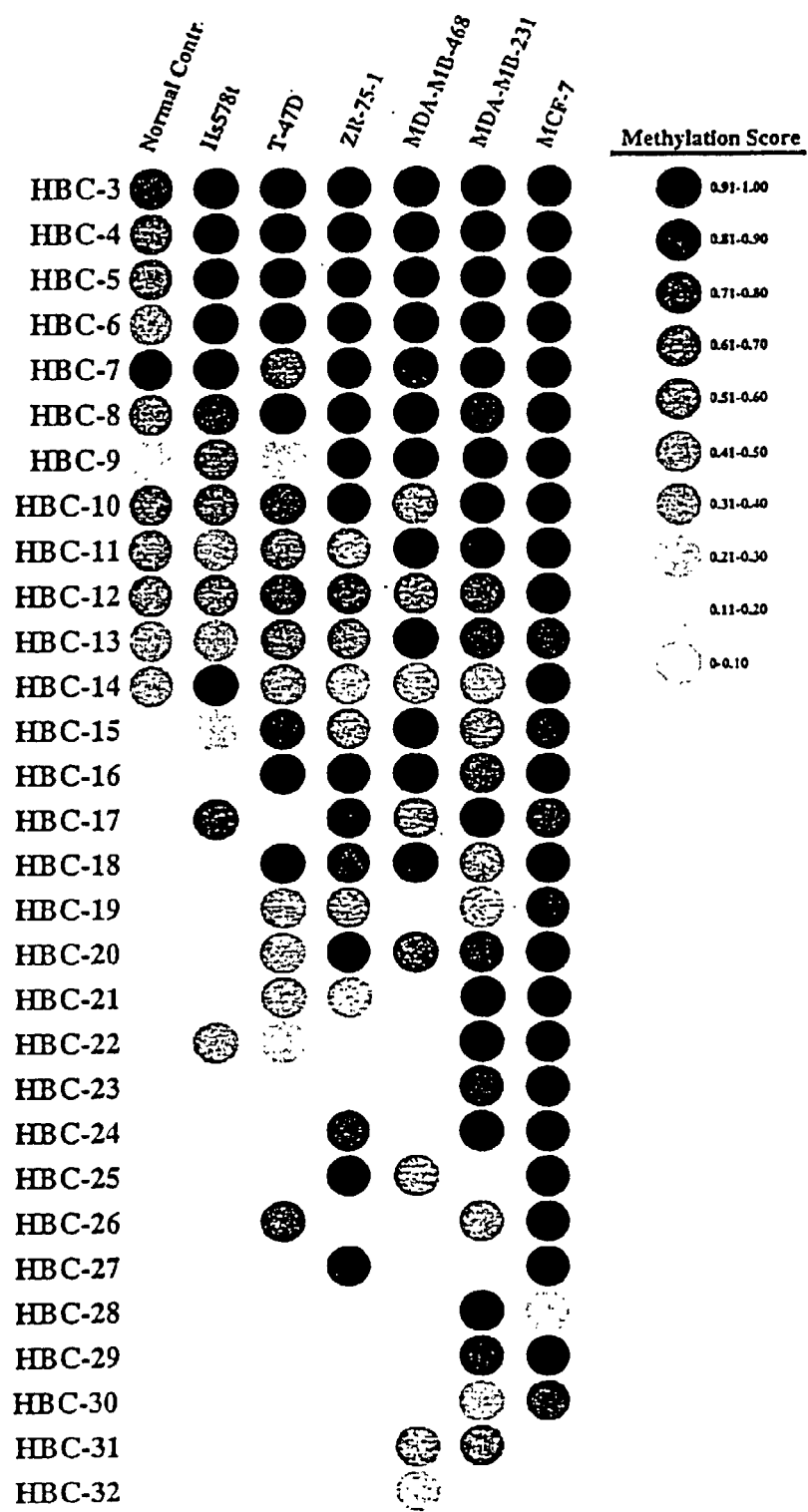
FIG. 7 is the methylation pattern analysis of 30 CpG island loci in breast cancer cell lines. Gray scales shown at right represent methylation scores of the 30 CpG island loci analyzed by Southern analysis (see examples in FIG. 5). The breast cancer cell lines indicated were arranged from left to right according to their increased methylation abilities (i.e., % of hypermethylated loci). The normal control was shown at the far left. Thirty CpG island loci (HBC-3 to -32) were listed from top to bottom according to their increased methylation scores derived from these cell lines.

Methylation scores of the 30 CpG island loci analyzed in the breast cancer cell lines and 1 normal control sample are summarized in FIG. 7. These cell lines are arranged from left to right according to their increased methylation abilities (i.e., % of hypermethylated loci), and the CpG island loci are listed from top to bottom according to their increased methylation scores derived from these cell lines. Methylation pattern analysis indicated that CpG islands might differ in their susceptibility to hypermethylation in these breast cancer cells. In loci HBC-3 to -15, various degrees of methylation at the tested BstU I sites were seen in the normal control sample. This pre-existing methylation condition was also observed in additional normal breast samples tested (data not shown). Hypermethylation of these loci appeared to be present and extensive in all the 6 cell lines examined. In contrast, hypermethylation in other loci (HBC-16 to -32) not displaying detectable pre-existing methylation in the normal control appeared to be less frequent in these cell lines. In some cases (e.g., HBC-23 to -32), hypermethylation was observed only in a few cell lines. This observation suggests that a trend exists in which CpG island loci associated with the pre-existing condition are inclined to de novo methylation in cancer cells. Pattern analysis also revealed that the overall methylation frequencies were varied among these cell lines. Methylation (methylation score greater than 0.1) was observed in 57% of these 30 loci in Hs578t, 67% in T47D, 77% in ZR-75-1, 80% in MDA-MB-468, 90% in MDA-MB-231, and 93% in MCF-7 cells, respectively. These differences were more obvious by comparing methylation patterns among the loci (HBC-16 to 32) not exhibiting the detectable pre-existing condition. In the two extreme cases, for example, only 4 of these 17 loci showed detectable methylation in Hs578t cells, whereas 15 of these loci had extensive methylation in MCF-7 cells. The results suggest that these cell lines differ in their intrinsic abilities to methylate CpG island sequences.

EXAMPLE 5

Methylation Analysis of Primary Breast Tumors by Southern Hybridization

Figure 8:
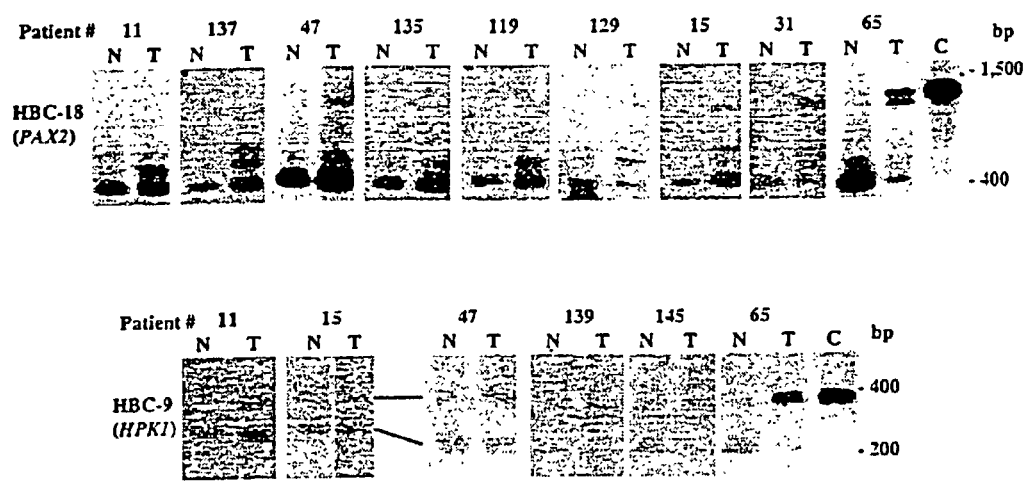
FIG. 8 is the methylation analysis of HBC-18 and -9 by Southern blot hybridization. Genomic DNA (10 mg) of breast tumor and the matching normal tissue was treated consecutively with Mse I and methylation-sensitive BstU I and subjected to Southern hybridization using the cloned genomic fragments as probes. These CpG island clones (HBC-18 and -19) contained sequences identical to the 5' end of PAX2 (paired box-containing gene 2) and the promoter and exon 1 of HPK1 (hematopoietic progenitor kinase gene 1), respectively. C: control DNA digested with Mse I only, T: breast tumor, and N: normal breast tissue. Patient numbers are shown at the top of lanes. Molecular weight markers (100 bp ladder; Promega) are shown at right.

It has been demonstrated that CpG islands associated with nonessential genes might become methylated over time in immortalized cells that have been in culture for many years. See Antequera et al., Cell 62: 503–514 (1990). We, therefore, determined whether our in vitro findings could represent bonafide de novo methylation in primary breast tumors. We validated the methylation status of 9 CpG island loci (HBC-6, -8, -9, -12, -15, -18, -20, -22, and -23) in primary breast tumors by Southern hybridization. As shown in FIG. 8, upper panel, HBC-18 was hypermethylated in the tumor DNA samples of patients 47, 135, 119, 129, 15, 31, and 65 relative to their paired normal breast tissue. Incomplete methylation of HBC-18 loci was detected in tumors of patients 11 and 137. In FIG. 8, lower panel, pre-existing methylation of HBC-9 was observed in the normal breast tissue of these patients consistent with the previous observation (FIG. 7). Hypermethylation of HBC-9 was observed in the tumor lanes of patients 47, 139, 145, and 65, showing increased band intensity of the 440-bp fragment relative to that of the same band in normal lanes. On preliminary observation, de novo methylation of two loci, HBC-16 and B26 was not present in 2 primary breast tumors (data not shown).

Comparisons of methylation patterns among the cell lines and a normal control indicate that the 30 CpG island loci might differ in their propensity for de novo methylation. This inherent condition may be at least in part influenced by a pre-existing methylation condition in local genomic sequences. As described in Example 4, loci HBC-3 to -15 seemed to be more susceptible to de novo methylation as compared to other loci (FIG. 7). Normal breast samples had detectable methylation in this group of CpG islands; methylation of these loci appeared to be extensive to complete in the cancer cell lines examined. In contrast, other loci without this pre-existing condition were less inclined to de novo methylation in breast cancer cells. This observation suggests that pre-existing methylation within a CpG island locus may promote subsequent de novo methylation in cancer cells.

This observation is further supported by several previous in vitro findings, showing that the activity of DNA-MTase could be positively influenced by a partial pre-methylation condition. See Christman et al., *Proc. Natl. Acad. Sci. USA*, 92: 7347–7351 (1995); Carotti et al., *Biochem. J.*, 37: 1101–1108 (1998). These studies found that single- or double-stranded synthetic polymers were poor substrates of the eukaryotic DNA-MTase, yet were efficiently methylated by the enzyme following the introduction of a small number of 5-methylcytosines by a prokaryotic methylase. Carotti et al. showed that the presence of 5-methylcytosines in double-stranded DNA substrates, either of natural or synthetic origins, stimulated in vitro methylation of neighboring CpG dinucleotides by DNA-MTase. Carotti et al., supra. The extent of stimulation depended both on the number and the distributions of the 5-methylcytosine residues, which could not be spaced too closely to exert the effect. This phenomenon has also been observed in human fibroblast cells transfected with a DNA-MTase cDNA. See Vertino et al., *Mol. Cell Biol.*, 16: 4555–4565 (1996). CpG island loci that were subject to de novo methylation in the transfected clones overexpressing DNA-MTase had low, but detectable levels of methylation in the parental lines. In contrast, CpG island loci found to be resistant to methylation in these transfected clones were devoid of methylation in the parental line.

This methylation-spreading phenomenon can account for the extensive methylation in CpG island loci with the pre-existing condition. It has been suggested that during tumorigenesis, pre-existing methylated repetitive elements may act as de novo methylation centers (i.e., cis-acting signals) from which methylation spreads into adjacent CpG island sequences. The results of these experiments indicate that methylation spread may actually occur from within a CpG island sequence in tumor cells. The existing 5-methylcytosine residues in the sequence may stimulate the de novo methylation function of DNA-MTase. Although DNA-MTase prefers hemimethylated substrates for its maintenance activity in normal cells, the enzyme may have a second regulatory domain "sensing" the presence of 5-methycytosines within CpG island sequences, allowing for de novo methylation. The "sensing" function could become more operative due to aberrantly high DNA-MTase levels in tumor cells. This may in turn lead to de novo methylation of cytosines located near sequences already containing methylated CpG dinucleotides. The newly methylated sites may acquire the ability to stimulate the subsequent methylation of adjacent sequences via DNA-MTase. This "domino"

effect of methylation could progress with time to include the entire CpG island region, leading to the associated transcriptional silencing.

Differential Methylation Abilities in Breast Cancer Cell Lines

A second characteristic of our findings was that these breast cancer cell lines exhibited differential methylation potentials. In the two extreme cases, Hs578t and MCF-7 cells, the former showed a lack of ability to methylate the CpG island group (HBC-16 to -32) without the pre-existing condition described above whereas the latter was proficient in methylating these CpG island loci. This suggests that the observed differences among these cell lines could not be solely due to the aberrant DNA-MTase action. The degrees of methylation appeared not to be correlated with the increased levels of DNMT1 expression or with the decreased levels of p21$^{WAF1}$ expression observed in these cells (FIGS. 1 and 7).

Thus, these results suggest that additional cellular factors may govern CpG island hypermethylation. One possibility may be an as yet unidentified or uncharacterized gene encoding a de novo methylase. Another possibility is that the various degrees of de novo methylation observed in these cancer cells might simply result from fixation of a hypermethylator phenotype that affords a greater proliferation potential. Finally, differential methylation abilities could be related to deficiencies in DNA repair in these cell lines.

EXAMPLE 6

DMH Screening of Breast Cancer Tumors

We have demonstrated the likelihood of potential mechanisms governing methylation in breast cancer cells by pattern analysis. DHM was then applied to determine whether patterns of specific epigenetic alterations correlate with pathological parameters in the patients analyzed.

Isolation of Amplicons from Breast Tumor DNA

DHM was used to analyze breast tumor specimens obtained from 28 female patients undergoing mastectomies at the Ellis Fischel Cancer Center (Columbia, Mo.) between 1992 and 1998. Adjacent, normal parenchyma was obtained from the same patient to serve as a normal control. All tumors used in this study were classified as infiltrating ductal carcinomas and were graded based on the Nottingham modified criteria of Bloom and Richardson. See Bloom, H. J. G. and Richardson, W. W., *Br. J. Cancer* 9: 359–377 (1957). This tumor-grading method was based on histological features of tubule formation, nuclear pleomorphism, and mitotic activity, and points were assigned for each category accordingly. The overall tumor grade was the sum total of scores between 3–9. Tumors with poorly differentiated phenotypes (8–9 points) are likely to have less or no tubular structures, irregular and large nuclei, and high mitotic counts. Tumors with moderately (6–7 points) or well differentiated (3–5 points) phenotypes may have definite tubule formation, moderate outlines of epithelial cell shapes and uniformity of nuclear chromatin, and low mitotic indexes. High-molecular-weight DNA was isolated from these specimens using QIAamp Tissue KitJ (Qiagen).

DMH was performed as provided in the materials and methods of Example 1. Genomic DNA (0.5–1 mg) from breast tumor or normal samples was utilized to prepare the amplicons as described in Example 1. The amplified products, labeled as normal or tumor amplicons, were purified and $^{32}$P-labeled for array hybridization. BstUI-positive, Cot-I-negative or -weakly positive CpG island clones were prepared from the CGI genomic library and used for 96-well format PCR as described in Example 1. Membranes were first hybridized with normal amplicons, and autoradiography was conducted using the Molecular Dynamics PhosphorImager. Probes were stripped and the same membranes, or duplicate membranes, were hybridized with tumor amplicons and scanned with the PhosphorImager.

Data Analysis

Dot intensities for positive CpG island tags were measured using the volume review protocol of ImageQuant software (Molecular Dynamics). The raw volume data from tumor and normal samples were normalized prior to comparison. This was achieved by ratio determination of the internal control tags. Briefly, two internal control tags with close volume ratios were selected to estimate hybridization differences between paired amplicons. One of these two control tags from each amplicon was further used to calculate a factor for normalization:

$$\text{Normalization factor} = \frac{\text{Normal internal control tag volume}}{\text{Tumor internal control tag volume}}$$

This factor was applied to normalize tumor tag volumes. For tags with preexisting methylation in normal tissue, the normal tag volume was subtracted from the normalized tumor volume. For tags without preexisting methylation in the normal tags, the normalized tumor volume was used directly. Statistical analyses were performed using the SigmaStat software (version 2.0). The hypermethylation differences among different groups of tumor grades were determined by the unpaired t-test and by the Mann-Whitney rank sum test when the data failed the normality test. The difference was considered significant when the P value was less than 0.05.

Results and Discussion

Figure 9:
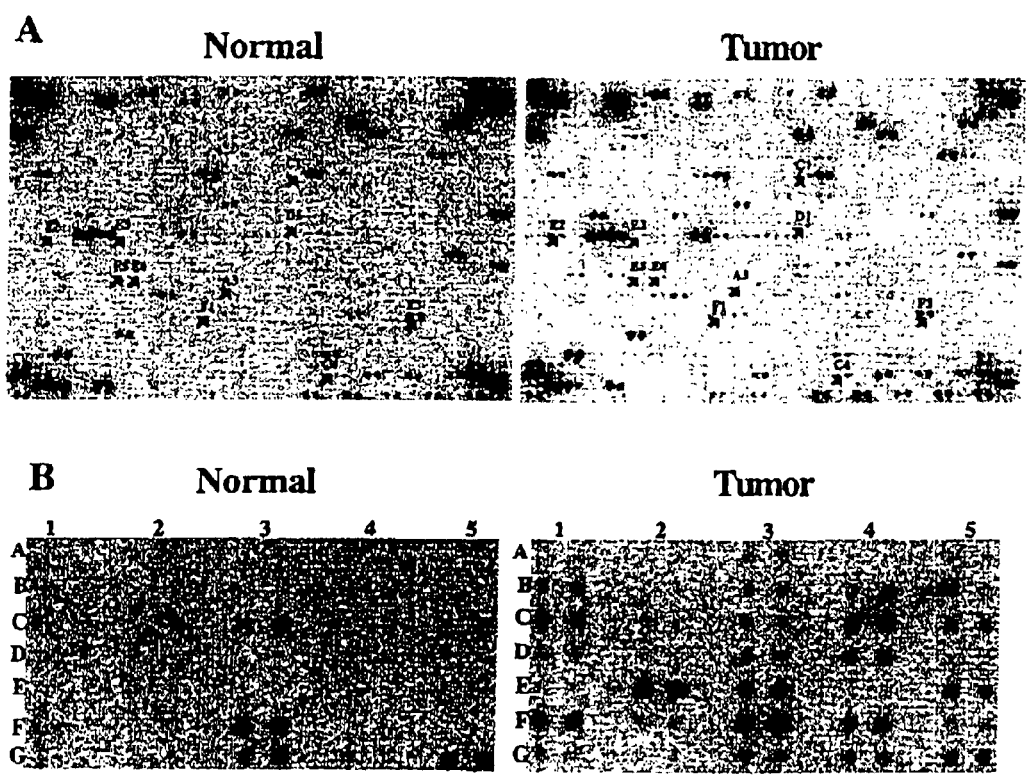
FIGS. 9A and 9B are representative results of differential methylation hybridization from one breast cancer patient.

DMH was initially applied to 28 paired breast tumor and normal samples using an array panel containing more than 1,000 CpG island tags. FIG. 9A shows representative results of DMH screening in paired normal and tumor samples of patient 103. Based on visual inspection, hypermethylated sequences were identified in breast tumors, showing detectable hybridization signals in CpG island tags probed with tumor amplicons, but not in the same tags probed with normal amplicons (see examples indicated by arrows). This is because methylated BstUI sites in tumor DNA were protected from restriction within CpG island sequences, which were then amplified by linker-PCR and hybridized to the corresponding tags. The same sites, however, were unmethylated or partially methylated in normal DNA and were restricted by BstUI; therefore, no hybridization signals were detected in the arrays. Some of these hypermethylated CGI island tags were confirmed in the subsequent secondary screening (FIG. 9B).

A few CpG island tags were detected by normal amplicons (i.e., preexisting methylation) but showed greater signal intensities when probed with tumor amplicons (e.g., CpG island tags on the lower right hand corner in FIG. 9A). These sequences usually exhibited more prominent hybridization signals among all of the tags, likely representing abundant copies of CpG dinucleotide rich ribosomal DNA as previously described in the cell line study. Methylation of ribosomal DNA has previously been observed in normal cells, but shown to increase to a greater extent in breast tumors. Another possibility is the increased copy numbers of normally methylated CpG island loci in tumors due to aneuploidy. Excluding this preexisting condition, the extent of hypermethylation in unmethylated CpG islands was quite variable among patients in this group; close to 9% of the tested BstUI sites exhibited complete methylation in some breast tumors examined while others had little or no detectable change in the tested sites.

Sequence Characterization of CpG Island Tags. Thirty CpG island tags positive for hypermethylation in the primary screening were selected for further characterization. DNA sequencing results showed that 9 of these tags contained sequences identical to known cDNAs, PAX7 (5' end), Caveolin-1 (exon2), GATA-3 (exon 1), and COL9A1 (exon 1), and 5 ESTs (AI928953, AA604922, AA313564, AI500696, and AI381934) as shown in Table 1.

This finding is consistent with that of Lisanti and coworkers where they also observed CpG island methylation in the Caveolin-1 gene in breast cancer cell lines. Five CpG island tags, HBC-17, 19, 24, 25, and 27, found to be hypermethylated in breast cancer cell lines as discussed in Example 5 were also identified in this study. The remainder twenty-five tags were numerically assigned as HBC-33 to -57.

Figure 10:
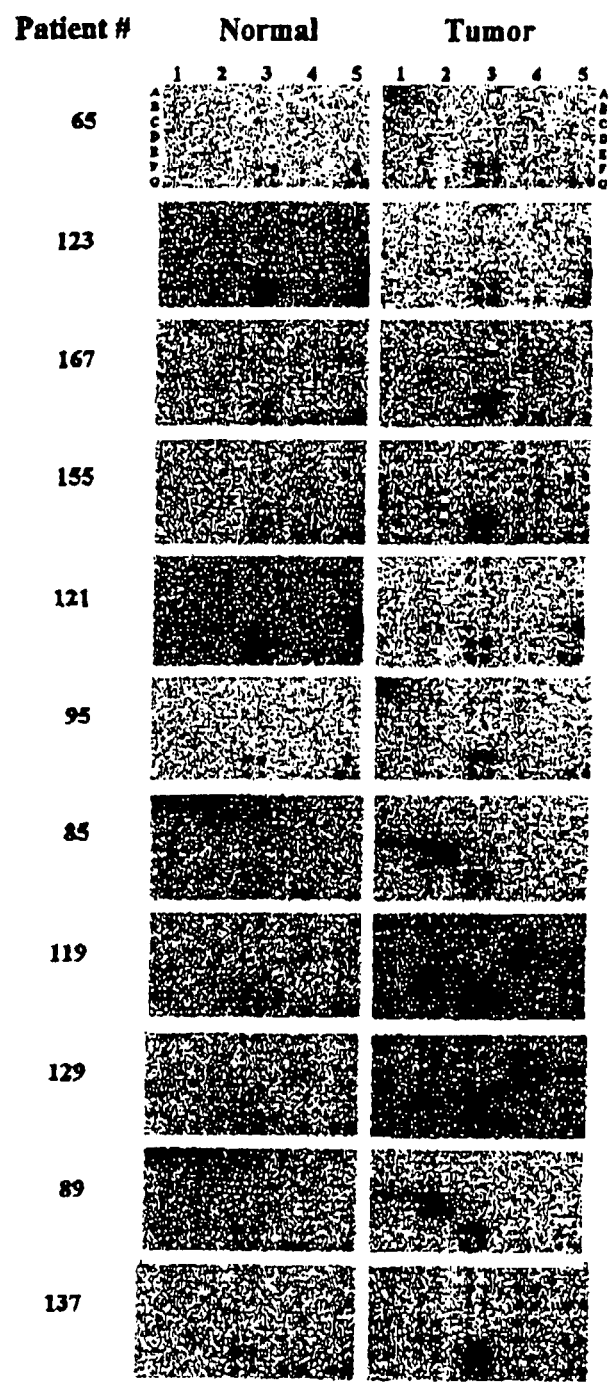
FIG. 10 represents the identification of hypermethylated CpG island loci by differential methylation hybridization. The 30 CpG island tags shown in this subarray panel were selected from an initial DMH screening of >1,000 tags. Five additional tags—coordinates on the x- and y-axes are 3C, 3F, 3G, 4G and 5G—were included as internal controls. CpG island tags were dotted onto membranes in duplicate and probed with radiolabeled amplicons for the normal and breast tumors as indicated. DMH screening from 11 of 28 patients were represented here, and experiments were performed independently at least twice.

Secondary Screening of DMH in Breast Tumors. As shown earlier in FIG. 9B, the 30 CpG island tags were rearrayed for secondary DMH screening in the patient group to confirm their hypermethylation status (see representative results in FIG. 10). Five additional tags—coordinates on the x- and y-axes are 3C, 3F, 3G, 4G, and 5G—showing no hybridization intensity differences among a few of the breast tumors tested in the primary screening were chosen as internal controls. Again, most normal controls showed few or no detectable hybridization signals at the tested loci, whereas the corresponding breast tumors exhibited various degrees of hybridization intensities, reflecting the differences in CpG island hypermethylation.

To semiquantify the methylation differences, hybridization signal intensity for each CpG island tag was measured using the volume review protocol of ImageQuant software as described in Materials and Methods. From FIG. 10, it is clear that dot intensities of the internal controls sometimes varied among patients or between a patient's paired tumor and normal samples, likely due to tissue heterogeneity or tumor aneuploidy. Therefore, internal control volume ratios were tested and two with close volume ratios were selected for normalization. The adjusted tumor volumes were used for clinical correlation in this patient group.

Figure 11:
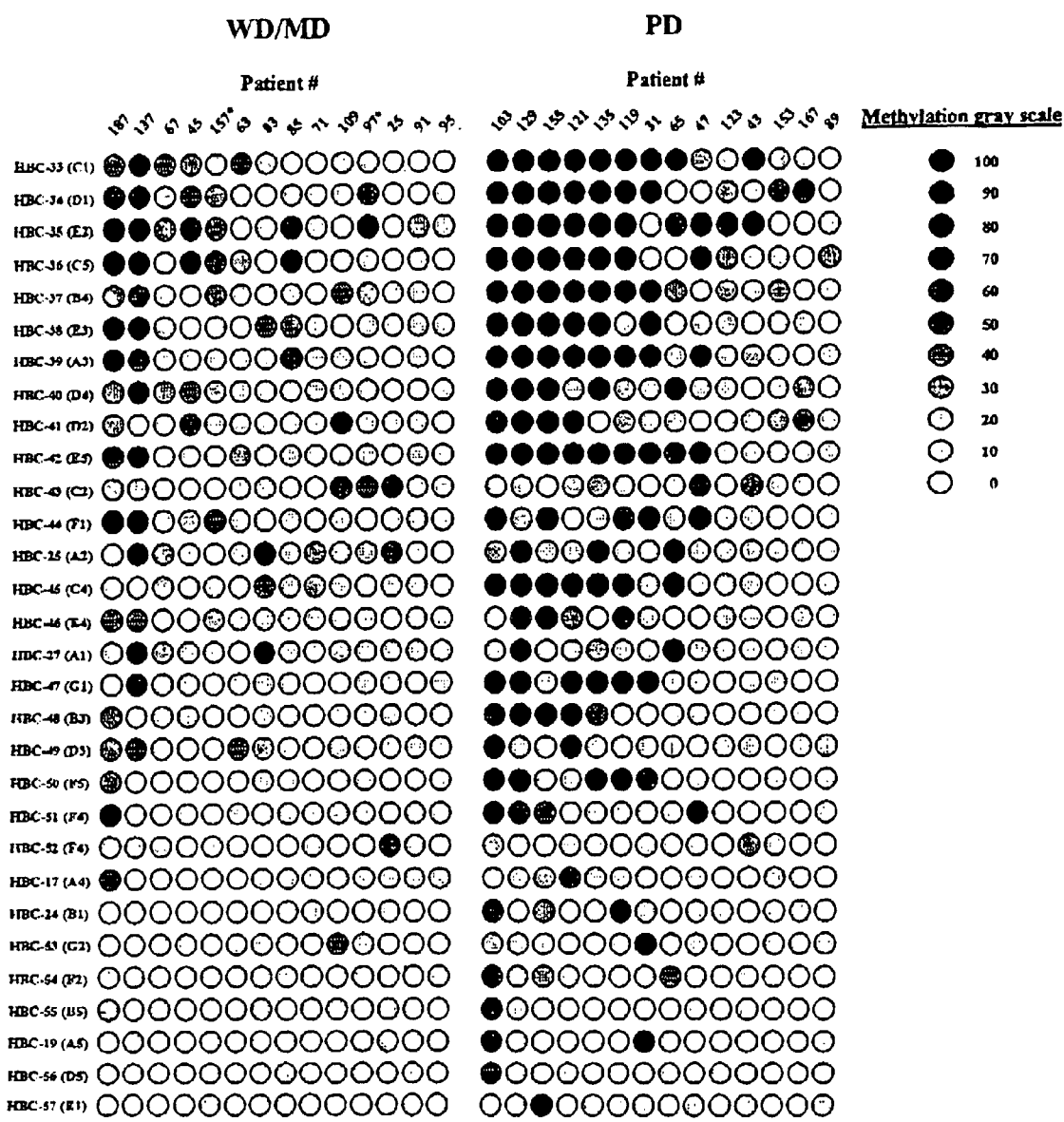
FIG. 11 represents the hypermethylation pattern analysis of 30 CpG island loci in 28 primary breast tumors. Methylation gray scale shown at the right represents volume percentile generated by ranking hybridization signal intensities of these tested loci. Data from primary tumors were presented according to their tumor grades: well-/moderately differentiated (WD/MD), and poorly differentiated (PD). Within each group, patients were arranged from left to right according to their increased methylation propensities. Thirty CpG island loci (on the left of the panel with their secondary screening coordinates shown in parenthesis) were listed from top to bottom according to their increased methylation scales derived from the primary tumors. Five CpG island loci (HBC-17, 19, 24, 25 and 27) were found to be hypermethylated in breast cancer cell lines.

CpG Island Hypermethylation and Tumor Grades. Statistical analysis revealed that CpG island hypermethylation was associated with histological grades of breast tumors (P-0.041). To aid in visualizing differences in CpG island hypermethylation among different tumor grades, we devised a gray scale by categorizing tumor methylation volumes into percentiles as depicted in FIG. 11. The PD[3] group exhibited more frequent and extensive hypermethylation at the loci tested than their MD/WD[3] counterparts did; half of the 14 PD tumors showed extensive hypermethylation at multiple loci (>10), while only two of the 14 MD/WD tumors showed hypermethylation at these loci. Moreover, the greatest degrees of differences were seen at loci HBC-42, -45, and -47 that were frequently hypermethylated in PD tumors, but not in MD/WD. This result suggests that patients with more advanced disease status are prone to methylation alterations. It should be noted that some of the patients showed little or no changes of methylation at the loci tested. This indicates that progression of some tumors may be independent of this epigenetic event or the alteration could occur in later stages of tumor development in such patients. No association of hypermethylation with other clinical parameters was found in this study.

The results of these experiments indicate that differential methylation patterns observed in various clinical specimens may reflect different stages or types of cancer. In this case, the most common methylation of CpG island loci (e.g., HBC-33, -34, -35, and -36) observed among different tumor grades likely occurs early during tumor development, while methylation groups (e.g., HBC-42, -45, and -47) observed preferentially in PD, but not in WD/MD groups, occur in later stages.

In view of the above, it will be seen that the several objects of the invention are achieved.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

TABLE 1

A list of positive CpG Island clones isolated by differential methylation hybridization

| CpG Island Clone | Insert Size (kb) | GenBank Match | ATCC Accession Number | SEQ ID ID NO |
|---|---|---|---|---|
| HBC-3 | 0.25 | | | 1 |
| HBC-4 | 0.90 | | | 2 |
| HBC-5 | 0.40 | DCISI | L27636 | 3 |
| HBC-6 | 0.80 | CGI Clone 28f11 | Z60565 | 4 |
| HBC-7 | 0.60 | CGI Clone 178c6 | Z59859 | 5 |
| HBC-8 | 0.38 | CGI Clone 200b9 | Z55140 | 6 |
| HBC-9 | 0.44 | HPK1 | U66464 | 7 |
| HBC-10 | 0.75 | K + Channel Protein | Z93016 | 8 |
| HBC-11 | 0.70 | | | 9 |
| HBC-12 | 0.50 | CGI Clone 86e9 | Z63556 | 10 |
| HBC-13 | 1.00 | CGI Clone 31g5 | Z60696 | 11 |
| HBC-14 | 0.70 | | | 12 |
| HBC-15 | 1.50 | CGI Clone 7c5 | Z66179 | 13 |
| HBC-16 | 1.00 | EST AA827755 | ESTAA827 | 14 |
| HBC-17 | 0.75 | | | 15 |
| HBC-18 | 1.30 | PAX2 | M89470 | 16 |
| HBC-19 | 0.90 | PAX7 | AL021528 | 17 |
| HBC-20 | 0.45 | CGI clone 67g9 | Z62363 | 18 |
| HBC-21 | 0.90 | | | 19 |
| HBC-22 | 0.45 | | | 20 |
| HBC-23 | 0.90 | | | 21 |
| HBC-24 | 1.10 | IMAGE:2518953 5'mRNA | AI928953 | 22 |
| HBC-25 | 0.70 | | | 23 |
| HBC-26 | 0.70 | GALNR2 | AF058762 | 24 |
| HBC-27 | 0.70 | | | 25 |
| HBC-28 | 0.60 | | | 26 |
| HBC-29 | 0.70 | | | 27 |
| HBC-30 | 0.80 | | | 28 |
| HBC-31 | 0.50 | EST 03867 | T05978 | 29 |
| HBC032 | 0.60 | EST 88248 | T35610 | 30 |
| HBC-34 | 0.95 | IMAGE:1113203 3'mRNA | AA604922 | 31 |
| HBC-37 | 1.00 | PAC 163M9 | AL021920 | 32 |
| HBC-38 | 0.50 | CGI 40c10 | Z58446 | 33 |
| HBC-39 | 0.60 | EST185442 | AA313564 | 34 |
| HBC-41 | 0.60 | CGI 29h6 | Z58110 | 35 |
| HBC-42 | 0.50 | CGI 13f7 | Z56764 | 36 |
| HBC-43 | 0.80 | Genomic Clone NH0444B04 | AC007392 | 37 |
| HBC-45 | 0.50 | PAC 29K1 | Z98745 | 38 |
| HBC-46 | 0.65 | IMAGE:2177671 3'mRNA | AI500696 | 39 |
| HBC-48 | 1.50 | BAC CLONE RG300E22 | AC004774 | 40 |
| HBC-49 | 0.50 | CGI 40c10 | Z58447 | 41 |

TABLE 1-continued

A list of positive CpG Island clones isolated by differential methylation hybridization

| CpG Island Clone | Insert Size (kb) | GenBank Match | ATCC Accession Number | SEQ ID ID NO |
|---|---|---|---|---|
| HBC-51 | 0.70 | COL9A1 (alt exon1) | M32133 | 42 |
| HBC-52 | 0.60 | IMAGE:2092259 3'mRNA | AI381934 | 43 |
| HBC-53 | 0.80 | Genomic Clone NH0444B04 | AC007392 | 44 |
| HBC-55 | 0.80 | CAVEOLIN-1 (exon2) | AF095592 | 45 |
| HBC-57 | 0.90 | GATA-3 (exon1) | X55122 | 46 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07144701B2). An electronic copy of the "Sequence Listing" will also be available from the USPTO upon request and payment of the fee set forth in 37 CFR 1.19(b)(3).

What is claimed is:

1. A process for detecting the presence or absence of methylation of CpG dinucleotide rich regions of nucleic acid sequences within a genomic DNA sample, the process comprising:
   a) contacting the genomic DNA sample with an enzyme that is not methylation-sensitive, lacks a CpG dinucleotide sequence in its recognition motif, and that cleaves the genomic DNA into fragments in which CpG islands are preserved and which have ends corresponding to the cleavage motif of the non-methylation-sensitive enzyme;
   b) ligating the fragments, via the ends corresponding to the cleavage motif of the non-methylation sensitive enzyme, to linker primers to form linker primer fragments;
   c) contacting the linker primer fragments with a methylation-sensitive enzyme which digests the linker primer fragments having unmethylated CpG dinucleotide sequences but not methylated CpG dinucleotide sequences to form a digestion product comprising methylated CpG island loci, and wherein fragments cleaved by the methylation-sensitive enzyme are rendered non-amplifiable by the linker primers;
   d) amplifying the digestion product to form amplicons of the methylated CpG island loci;
   e) labeling the amplicons;
   f) contacting the labeled amplicons with a screening array comprising a plurality of nucleic acid fragments affixed to a solid support; and
   g) determining the presence or absence of labeled amplicons bound to the plurality of nucleic acid fragments affixed to the solid support of the screening array to thereby detect the presence or absence of methylation of a CpG dinucleotide rich regions.

2. The process of claim 1 wherein the plurality of nucleic acid fragments affixed to the solid support of the screening array are derived from a CpG dinucleotide rich genomic library.

3. The process of claim 2 wherein the plurality of nucleic acid fragments affixed to the solid support of the screening array are CpG dinucleotide rich fragments which comprise a sequence of at least about 200 nucleotides of which at least about 50% are guanine and cytosine.

4. The process of claim 3 wherein at least 20 nucleic acid fragments are affixed to the solid support of the screening array.

5. The process of claim 3 wherein the plurality of nucleic acid fragments affixed to the solid support of the screening array each contain a promoter and a first exon of a gene.

6. The process of claim 5 wherein the plurality of nucleic acid fragments affixed to the solid support of the screening array each comprise a nucleic acid sequence which is expressed in an organism.

7. The process of claim 6 wherein at least 20 nucleic acid fragments are affixed to the solid support of the screening array.

8. The process of claim 7 wherein at least 100 nucleic acid fragments are affixed to the solid support of the screening array.

9. The process of claim 8 wherein at least 500 nucleic acid fragments are affixed to the solid support of the screening array.

10. The process of claim 1 wherein the solid support of the screening array comprises nylon, glass or silicon.

11. The process of claim 1 wherein the label is selected from the group consisting of radioisotopes and fluorescent labels.

12. The process of claim 1 wherein the enzyme is selected from the group consisting of MseI, Tsp509I, NlaIII and BfaI and the methylation sensitive enzyme is selected from the group consisting of BstU I, SmaI, SacII, EagI, MspI, HpaII, HhaI and BssHII.

13. The process of claim 12 wherein the enzyme is MseI and the methylation sensitive enzyme is BstU I.

14. The process of claim 1 wherein said process is used for diagnosing and monitoring the prognosis of a disease associated with aberrant DNA methylation.

15. The process of claim 14 wherein said disease is breast cancer, prostate cancer, colon cancer, lung cancer, liver cancer and ovarian cancer.

16. The process of claim 15 wherein the disease is breast cancer.

17. The process of claim 16 wherein the CpG island fragments affixed on the solid support of the screening array comprise a fragment corresponding to SEQ ID NO:36.

* * * * *